(12) United States Patent
Mauduit et al.

(10) Patent No.: US 9,776,178 B2
(45) Date of Patent: Oct. 3, 2017

(54) RUTHENIUM COMPLEXES COMPRISING AN ASYMMETRICAL UNSATURATED N-HETEROCYCLIC DIAMINOCARBENE

(71) Applicants: Ecole Nationale Superieure de Chimie de Rennes, Rennes (FR); Centre National de la Recherche Scientifique CNRS, Paris (FR)

(72) Inventors: Marc Mauduit, Vitre (FR); Mathieu Rouen, Muids (FR)

(73) Assignees: Ecole Nationale Superieure De Chimie De Rennes, Rennes (FR); Centre National De La Recherche Scientifique CNRS, Paris (FR)

( * ) Notice: Subject to any disclaimer, the term of this patent is extended or adjusted under 35 U.S.C. 154(b) by 0 days.

(21) Appl. No.: 14/651,243

(22) PCT Filed: Dec. 11, 2013

(86) PCT No.: PCT/FR2013/053037
§ 371 (c)(1),
(2) Date: Jun. 11, 2015

(87) PCT Pub. No.: WO2014/091157
PCT Pub. Date: Jun. 19, 2014

(65) Prior Publication Data
US 2015/0315223 A1    Nov. 5, 2015

(30) Foreign Application Priority Data

Dec. 12, 2012 (FR) ...................................... 12 61971

(51) Int. Cl.
*C07F 15/00*    (2006.01)
*B01J 31/22*    (2006.01)

(52) U.S. Cl.
CPC ....... *B01J 31/2273* (2013.01); *B01J 31/2278* (2013.01); *C07F 15/0046* (2013.01); *B01J 2231/543* (2013.01); *B01J 2531/821* (2013.01)

(58) Field of Classification Search
CPC ................................................ C07F 15/0046
See application file for complete search history.

(56) References Cited

U.S. PATENT DOCUMENTS

2006/0287450 A1* 12/2006 Kohler ................ B01J 31/1608
526/176

OTHER PUBLICATIONS

Jafarpour et al. "Indenylidene—Imidazolylidene Complexes of Ruthenium as Ring-Closing Metathesis Catalysts" Organometallics, 1999, vol. 18, pp. 5416-5419.*
Samojlowicz et al. "Ruthenium-Based Olefin Metathesis Catalysts Bearing N-Heterocyclic Carbene Ligands" Chemical Reviews, 2009, vol. 109, pp. 3708-3742.*
Arduengo et al. "Electronic stabilization of nucleophilic carbenes" Journal of the American Chemical Society, 1992, vol. 114, pp. 5530-5534.*
CAS Accession No. 2005:158584.*
Ledoux et al. "N,N'-dialkyl- and N-alkyl-N-mesityl-substituted N-heterocyclic carbenes as ligands in Grubbs catalysts", Chemistry—A European Journal (2006), 12(17), 4654-4661.*
Article—Fürstner et al., "Convenient, scalable and flexible method for the preparation of imidazolium salts with previously inaccessible substitution patterns," *Chem. Commun.*, 2006, pp. 2176-2178.
Article—Ledoux et al, "Comparative Investigation of Hoveyda-Grubbs Catalysts bearing Modified N-Heterocyclic Carbene Ligands," *Adv. Synth. Catal.*, vol. 349, 2007, pp. 1692-1700.
Article—Samojlowicz et al., "Ruthenium-Based Olefin Matathesis Catalysts Bearing N-Heterocyclic Carbene Ligands," *Chem. Rev.*, vol. 109, 2009, pp. 3708-3742.
International Search Report for PCT/FR2013/053937 dated Feb. 17, 2014, 3 pages.
Article—Li et al., "Synthesis of unsymmetrical imidazolium salts by direct quaternization of N-substituted imidazoles using arylboronic acids," *Chem. Commun.*, 2014, vol. 50, pp. 3941-3943.

* cited by examiner

*Primary Examiner* — Joseph Kosack
(74) *Attorney, Agent, or Firm* — Dority & Manning, P.A.

(57) ABSTRACT

The invention relates to a ruthenium alkylidene complex comprising a 1-aryl-3-cycloalkyl-imidazolin-2-ylidene ligand, the cycloalkyl group of said 1-aryl-3-cycloalkyl-imidazolin-2-ylidene ligand being a cyclic secondary aliphatic alkyl.

12 Claims, 9 Drawing Sheets

RUTHENIUM COMPLEXES COMPRISING AN ASYMMETRICAL UNSATURATED N-HETEROCYCLIC DIAMINOCARBENE

CROSS REFERENCE TO RELATED APPLICATION

This application is the national stage entry of International Patent Application No. PCT/FR2013/053037 having a filing date of Dec. 11, 2013, which claims priority to and the benefit of French Patent No. 1261971 filed in the French Intellectual Property Office on Dec. 12, 2012, the entire contents of which are incorporated herein by reference.

The present invention relates to asymmetric imidazolium salts and the method of preparation thereof.

The N-heterocyclic diaminocarbenes (NHC, N-heterocyclic carbene) are ligands that are used extensively in organometallic catalysis. This is because the N-heterocyclic diaminocarbene ligands can form highly reactive species when they are associated with a metal. These species are then called diaminocarbene metal complexes.

Among the numerous ligands, we may notably mention the ligands of the imidazolidin-2-ylidene type (saturated NHC), and the ligands of the imidazolin-2-ylidene type (unsaturated NHC). In fact, with a metal, these ligands form complexes that are particularly suitable for organometallic catalysis. The publications *NHCs in Synthesis*, S. P. Nolan, Ed., 2006, Wiley-VCH; *NHCs in Transition Metal Catalysis*, F. Glorius, Ed. 2006, Springer; *N-Heterocyclic Carbenes*, S. D. Diez-Gonzalez, Ed. 2011, RSC Catalysis Series, RSC Publishing, disclose diaminocarbene metal complexes of this type.

It has now been demonstrated that the diaminocarbene metal complexes not only make it possible to increase the yield of certain chemical reactions, but also to perform new chemical reactions that were previously unknown. The diaminocarbene metal complexes have made it possible, for example, to improve the yields of the majority of metal-catalysed reactions, and notably in C—C, C—N, C—O, C—S coupling reactions etc. These coupling reactions are widely used in industrial processes in fine chemistry, as described in the work by Dunetz et al., Chem. Rev. 2011, 111, 2177-2250.

However, it is certainly in the metathesis of olefins that metals bearing N-heterocyclic diaminocarbene ligands have contributed most in terms of improving reaction yields, while allowing significant reductions in the amount of catalyst that is necessary and sufficient for catalysing the reaction. This is notably reported in Grela et al., Chem. Rev. 2009, 109, 3708-3742.

In general, the prior art shows that it is symmetric 1,3-disubstituted diaminocarbene imidazolidin-2-ylidene or imidazolin-2-ylidene ligands that are involved in the organometallic catalytic systems (cf. publications cited above).

Nevertheless, certain disclosures show that 1,3-disubstituted diaminocarbene imidazolidin-2-ylidene or imidazolin-2-ylidene ligands that are asymmetric, and therefore bear non-identical carbon-containing groups, can also be involved in organometallic catalytic systems. Thus, the work of Blechert et al., Dalton Trans. 2012, 41, 8215-8225 shows good reactivities and selectivities for asymmetric carbene ligands. The work by Grubbs et al., J. Am. Chem. Soc. 2011, 113, 7490-7496 shows, moreover, that good reactivities and selectivities can be observed when an N-heterocyclic diaminocarbene ligand bears an aromatic substituent on the one hand and an alkyl group on the other hand.

However, the nature and choice of the carbon-containing groups as substituents are still very limited in regard to the asymmetric 1,3-disubstituted diaminocarbene imidazolin-2-ylidene ligands. This is due in particular to the difficulty of synthesizing the asymmetric imidazolium precursor salts.

In fact, to synthesize an asymmetric 1,3-disubstituted diaminocarbene imidazolin-2-ylidene ligand it is crucial to generate an imidazolium precursor salt first. This synthesis is complex and requires either a very large number of chemical operations (4 to 6 separate chemical operations), or a limited prior choice of carbon-containing substituent groups.

The work by Organ et al., Angew. Chem. Int. Ed., 2007, 46, 2768-2813, and the work by Cbsar et al. Chem. Rev. 2011, 111, 2701-2733 show the complexity and the limits of synthesis of asymmetric 1,3-disubstituted diaminocarbene imidazolin-2-ylidene ligands.

The asymmetric 1,3-disubstituted diaminocarbene imidazolin-2-ylidene ligands are of considerable scientific and economic interest, but so far their synthesis is not industrially competitive notably because the number of chemical operations is far too high. Moreover, there is a limited choice of non-identical substituent groups.

Quite particularly, the prior art does not describe any suitable method for synthesizing N-heterocyclic diaminocarbene ligands of the 1-aryl-3-cycloalkyl-imidazolin-2-ylidene type (namely NHCs substituted on the one hand with an aromatic group, and on the other hand with a cyclic secondary aliphatic alkyl group). It goes without saying that the prior art does not describe diaminocarbene metal complexes bearing these ligands.

The invention will improve this situation.

Thus, the invention relates to an alkylidene ruthenium complex comprising a 1-aryl-3-cycloalkyl-imidazolin-2-ylidene ligand, characterized in that the cycloalkyl group of said 1-aryl-3-cycloalkyl-imidazolin-2-ylidene ligand is a cyclic secondary aliphatic alkyl.

The alkylidene ruthenium complex can be of general formula selected from the group consisting of formula 1,

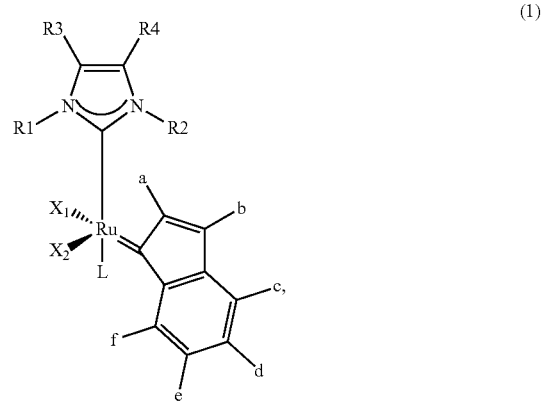

in which
R1 is an aromatic group,
R2 is a cyclic secondary aliphatic alkyl group,
R3 and R4 are selected independently of one another from the group consisting of a hydrogen atom, a halide and an alkyl group,
$X_1$ and $X_2$ are anionic ligands,
L is an uncharged ligand, and a, b, c, d, e and f are selected independently of one another from the group consisting of a hydrogen atom, an alkyl group and a heteroalkyl group;
of formula 2:

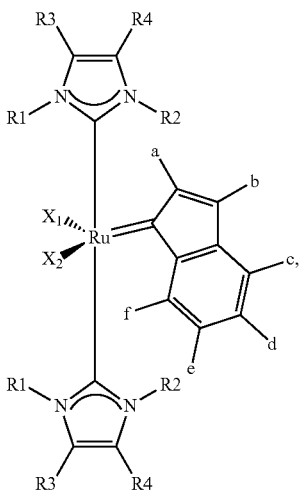

(2)

in which
R1 is an aromatic group,
R2 is a cyclic secondary aliphatic alkyl group,
R3 and R4 are selected independently of one another from the group consisting of a hydrogen atom, a halide and an alkyl group,
$X_1$ and $X_2$ are anionic ligands, and
a, b, c, d, e and f are selected independently of one another from the group consisting of a hydrogen atom, an alkyl group and a heteroalkyl group;
of formula 3:

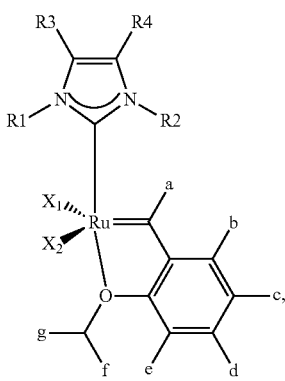

(3)

in which
R1 is an aromatic group,
R2 is a cyclic secondary aliphatic alkyl group,
R3 and R4 are selected independently of one another from the group consisting of a hydrogen atom, a halide and an alkyl group,
$X_1$ and $X_2$ are anionic ligands, and
a, b, c, d, e, f and g are selected independently of one another from the group consisting of a hydrogen atom, an alkyl group and a heteroalkyl group;

and of formula 4:

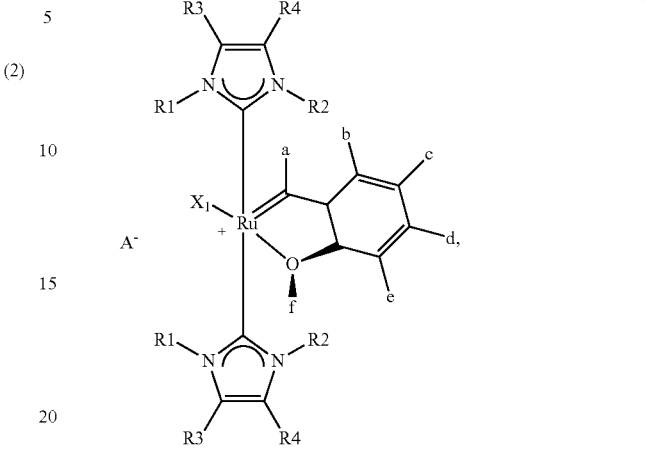

(4)

in which
R1 is an aromatic group,
R2 is a cyclic secondary aliphatic alkyl group,
R3 and R4 are selected independently of one another from the group consisting of a hydrogen atom, a halide and an alkyl group,
a, b, c, d, e and f are selected independently of one another from the group consisting of a hydrogen atom, an alkyl group and a heteroalkyl group,
$X_1$ is an anionic ligand, and
$A^-$ is an anion.

R1 can be selected from the group consisting of 2,4,6-trimethylphenyl, 3,5-dinitrophenyl, 2,4,6-tris(trifluoromethyl)phenyl, 2,4,6-trichlorophenyl, and hexafluorophenyl. R2 can be selected from the group consisting of cyclopentyl, cyclohexyl, cycloheptyl, cyclooctyl, cyclodecyl, cyclododecyl, and cyclopentadecyl. R3 and R4 are preferably each a hydrogen atom.

The invention also relates to the use of an alkylidene ruthenium complex as defined above as a catalyst in an olefin metathesis reaction.

Moreover, the invention relates to a method of preparing an alkylidene ruthenium complex comprising the following steps:
a. forming a first reaction mixture by contacting an imidazolium salt of formula 1S:

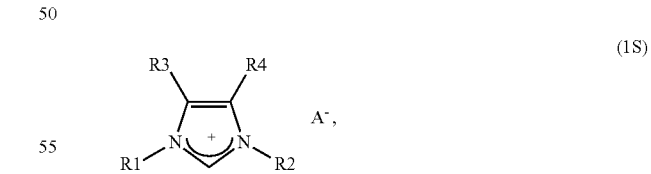

(1S)

in which
R1 is an aromatic group,
R2 is selected from a cyclic secondary aliphatic alkyl group and a heteroalkyl group,
R3 and R4 are selected independently of one another from the group consisting of a hydrogen atom, a halide and an alkyl group, and
$A^-$ is an anion,
with a strong base, in a solvent, under inert atmosphere, at room temperature, for at least 30 minutes;

b. adding a ruthenium complex precursor to the reaction mixture formed in step a., and then heating at a temperature of at least 40° C. for at least 2 hours;
c. isolating an alkylidene ruthenium complex.

Step b. can be carried out at a temperature of about 80° C. and the ruthenium complex precursor added in this step can be of formula 1P:

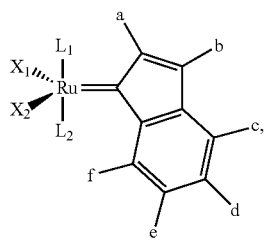

(1P)

in which, $X_1$ and $X_2$ are anionic ligands, $L_1$ and $L_2$ are uncharged ligands, preferably of tricyclohexylphosphine, and a, b, c, d, e and f are selected independently of one another from the group consisting of a hydrogen atom, an alkyl group and a heteroalkyl group.

In one embodiment, the method further comprises the following step d.:

d. forming a second reaction mixture by contacting the alkylidene ruthenium complex isolated in step c. with a styrenyl ether.

Step b. can be carried out for at least 3 hours and the ruthenium precursor complex can be of the so-called first-generation Hoveyda-Grubbs type.

In a preferred embodiment of the invention, the styrenyl ether is of formula 4H:

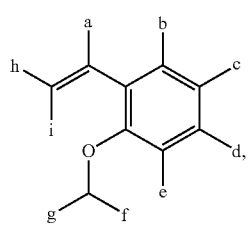

(4H)

in which a, b, c, d, e, f, g, i and h are selected Independently of one another from the group consisting of a hydrogen atom, an alkyl group and a heteroalkyl group.

Other advantages and features of the invention will become clear on reading the detailed description given below and from the appended drawings in which.

Figure 16:
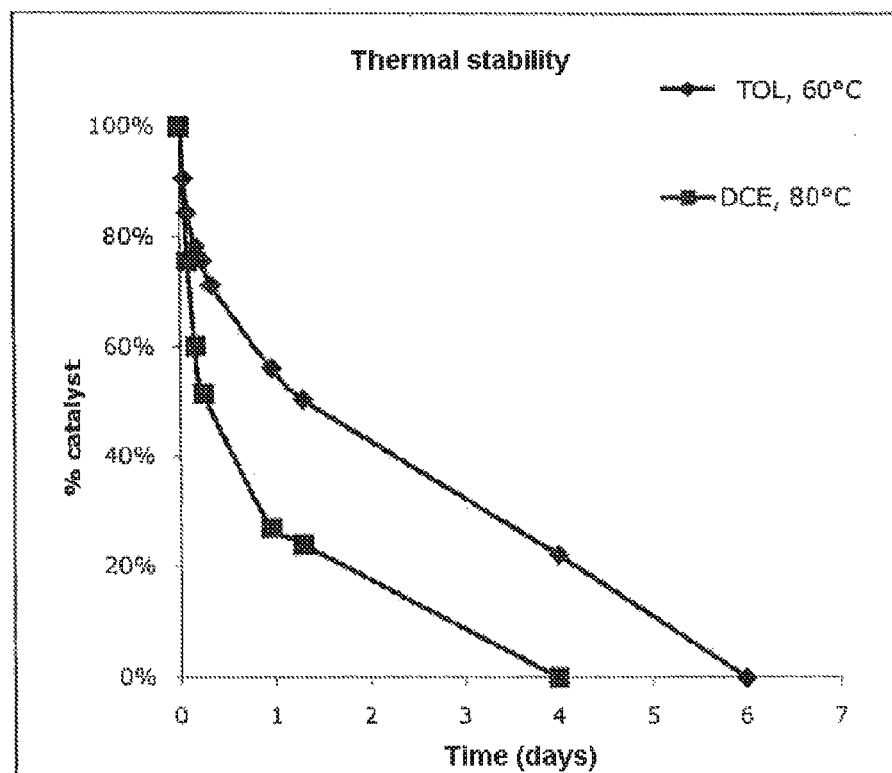
Figure 17:
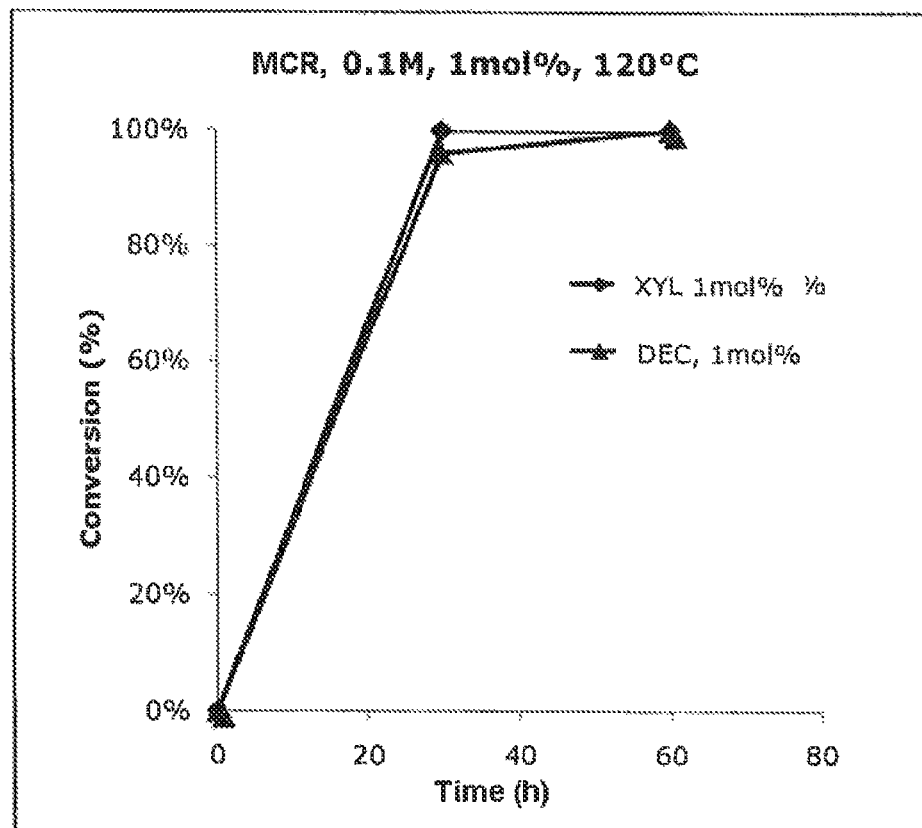

FIG. 16 shows the thermal stability of an alkylidene ruthenium complex according to the invention of formula 4.1, at 60° C., and at 80° C.; and FIG. 17 shows the catalytic activity of an alkylidene ruthenium complex according to the invention of formula 4.1 at 1 mol % in a metathesis cyclization reaction (MCR) of diethyl 2,2-diallylmalonate at 120° C., in xylene (XYL) and in diethyl carbonate (DEC).

The drawings and the following description contain, essentially, elements of a definite character. Therefore they can serve not only for better comprehension of the present invention, but can also contribute to its definition, if applicable.

The synthesis of an alkylidene ruthenium complex according to the invention comprises a preliminary step of synthesis of an asymmetric imidazolium salt of formula 1S:

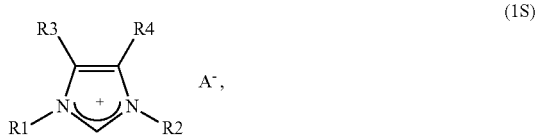

in which R1 is an aromatic group, R2 is selected from a cyclic secondary aliphatic alkyl group, R3 and R4 are selected independently of one another from the group consisting of hydrogen, a halide and an alkyl group, and $A^-$ is an anion.

The synthesis of this salt is carried out in a single operation and comprises the following steps:
  a. forming a reaction mixture by contacting one equivalent (1 eq) of an aniline of formula 2S:

with one equivalent (1 eq) of a compound of formula 3S:

in the presence of at least four point five equivalents (4.5 eq) of a Brønsted acid of formula 4S:

b. forming a solution comprising one equivalent (1 eq) of a dicarbonyl of formula 5S:

one equivalent (1 eq) of formaldehyde, and at least four point five equivalents (4.5 eq) of the Brønsted acid of formula 4, heating said solution to about 80° C. and then adding the reaction mixture formed in step a.;
  c. stirring for at least 2 hours at about 80° C.; and
  d. isolating the asymmetric imidazolium salt of formula 1S.

This synthesis therefore makes it possible to obtain, in a single chemical operation, a 1,3-disubstituted imidazolium salt bearing an aromatic group on the one hand, and a cycloalkyl group on the other hand.

The Brønsted acid of formula 4S can notably be acetic acid. This supplies a counter-ion $A^-$ of the acetate type.

The selectivity of the reaction of synthesis of the 1,3-disubstituted imidazolium salt can reach a ratio of 1/30/1 in favour of the desired asymmetric imidazolium salt (more precisely: 1 part of the first symmetric salt, 1 part of the second symmetric imidazolium salt, and 30 parts of the asymmetric imidazolium salt). In fact, the applicants discovered that when an aromatic amine and an aliphatic amine are brought in contact in the conditions described above, their difference in reactivity minimizes the formation of 1,3-bis-aryl and 1,3-bis-alkyl imidazolium salts, which are by-products of the reaction resulting from a reaction of auto-condensation of the amines present in the reaction mixture.

To make the asymmetric imidazolium salt more stable (or more reactive notably towards the ruthenium complex precursors), it is envisaged to supply a counter-ion $A^-$ selected from the group consisting of a tetrafluoroborate anion, a hexafluorophosphate anion, a hexafluoroantimony anion, a tetrakis[(3,5-trifluoromethyl)phenyl]borate anion and a halide anion. It is therefore advantageous to provide an exchange of counter-ion.

For this, steps a. to d. described above are followed by the following steps e. to f.:
  e. adding one equivalent (1 eq) of an inorganic salt and of the organic solvent, preferably dichloromethane, to the asymmetric imidazolium salt isolated in step d.;
  f. stirring at room temperature for at least one hour and carrying out a water/organic solvent extraction followed by evaporation of said organic solvent;
  g. precipitating with a polar organic solvent, and then isolating the asymmetric imidazolium salt of formula 1B.

The inorganic salt in step e. is selected from the group consisting of potassium tetrafluoroborate, sodium tetrafluoroborate, lithium tetrafluoroborate, hydrogen tetrafluoroborate, ammonium tetrafluoroborate, potassium hexafluorophosphate, sodium hexafluorophosphate, lithium hexafluorophosphate, hydrogen hexafluorophosphate, ammonium hexafluorophosphate, silver hexafluoroantimony, potassium hexafluoroantimony, sodium hexafluoroantimony, lithium hexafluoroantimony, potassium tetrakis[(3,5-trifluoromethyl)phenyl]borate, sodium tetrakis[(3,5-trifluoromethyl)phenyl]borate and lithium tetrakis[(3,5-trifluoromethyl)phenyl]borate and halogen acid.

This makes it possible to obtain a suitable counter-ion $A^-$.

According to various embodiments envisaged, R1 is selected from the group consisting of 2,4,6-trimethylphenyl, 3,5-dinitrophenyl, 2,4,6-tris(trifluoromethyl)phenyl, 2,4,6-trichlorophenyl, and hexafluorophenyl; and R2 is selected from the group consisting of cyclopentyl, cyclohexyl, cycloheptyl, cyclooctyl, cyclodecyl, cyclododecyl, and cyclopentadecyl. Selection from these groups provides good steric stability firstly of the salt, and secondly of the ruthenium complex, as will be seen below.

Taking as an example a group R1 of 2,4,6-trimethylphenyl, a group R2 of cyclohexyl and groups R3 and R4 of hydrogen, and following the method described above, a 1-aryl-3-cycloalkyl-imidazolin-2-ylidene of the following formula 65 is obtained:

Reaction scheme I: synthesis of intermediate asymmetric imidazolium salt in which R1 is 2,4,6-trimethylphenyl and R2 is cyclohexyl

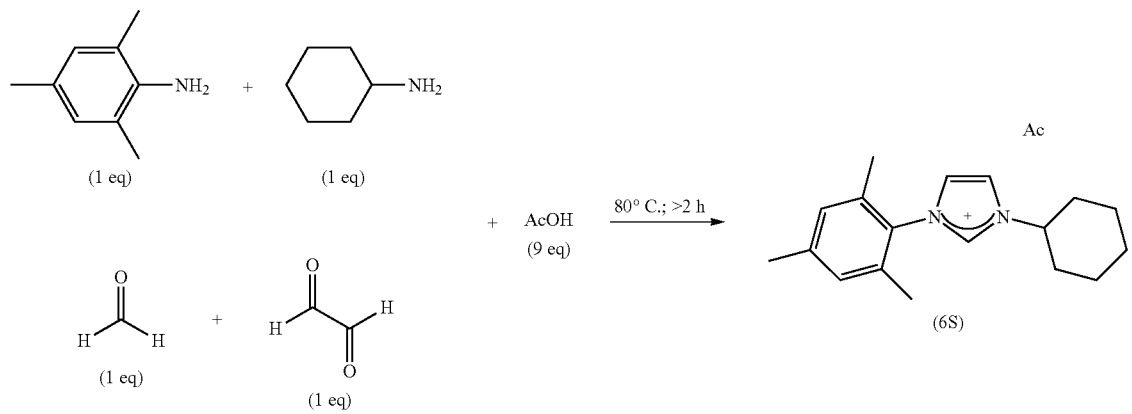

To determine the selectivity of the reaction, the reaction mixture comprising the 1-aryl-3-cycloalkyl-imidazolin-2-ylidene salt of formula 65 is cooled to room temperature. Then water is added, followed by solvent (for example in ethyl acetate or dichloromethane). The aqueous phase is extracted (for example three times) with the solvent. The organic phases are combined and dried over an anionic salt (for example over magnesium sulphate). Then the organic phase is concentrated under vacuum. Nuclear magnetic resonance (NMR) analysis of the crude reaction product can provide determination of the selectivity of the reaction.

Exchange of the acetate anion against another anion, in order to make the salt more stable or more reactive, can be carried out as follows: the crude reaction product is dissolved in solvent (for example dichloromethane). Then 1 equivalent of the inorganic salt comprising the desired counter-anion is added (for example potassium tetrafluoroborate to obtain a tetrafluoroborate counter-anion). The mixture is then stirred at room temperature for some hours (for example 3h). Then a liquid/liquid extraction is carried out, namely a water/organic solvent extraction. For this, water is added and the organic phase is separated from the aqueous phase. The aqueous phase is washed (for example three times) with solvent. Each organic phase is dried over an anionic salt (for example over magnesium sulphate), and concentrated under vacuum. Generally a brown oil is obtained, to which an organic solvent is added for precipitation (for example ethyl acetate). Then the mixture can be submitted to ultrasonic treatment for some minutes (for example 5 minutes). A solid forms, which is filtered on a frit, then washed with solvent (for example with ethyl acetate) to give the desired asymmetric imidazolium with a desired anion (for example a tetrafluoroborate anion).

In general, the aforementioned precipitation with a polar organic solvent can be performed using ethyl acetate, diethyl ether, or crystallization in ethanol. Precipitation with ethyl acetate is preferably used.

With the above operating procedure, which only comprises a single chemical operation, the applicants were able to synthesize a large number of salts. Notably, the applicants synthesized the asymmetric imidazolium salts of formula 7S, 8S, 9S, 10S, 11S, 12S, 13S, 14S, 15S, 16S, 17S and 18S:

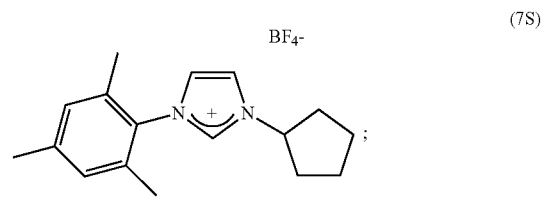

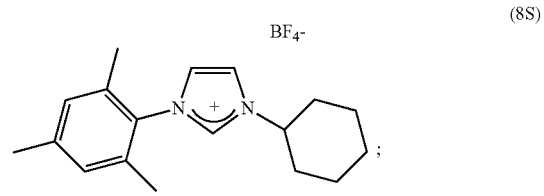

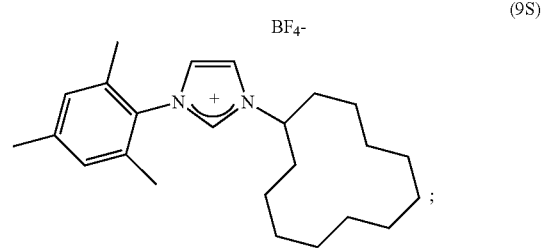

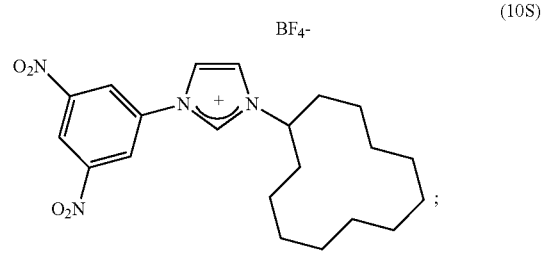

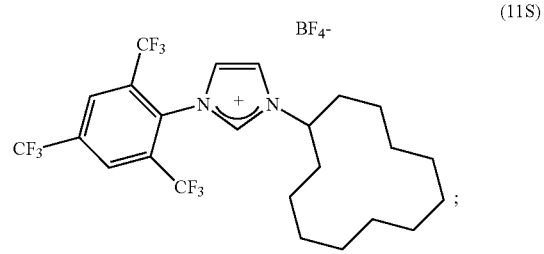

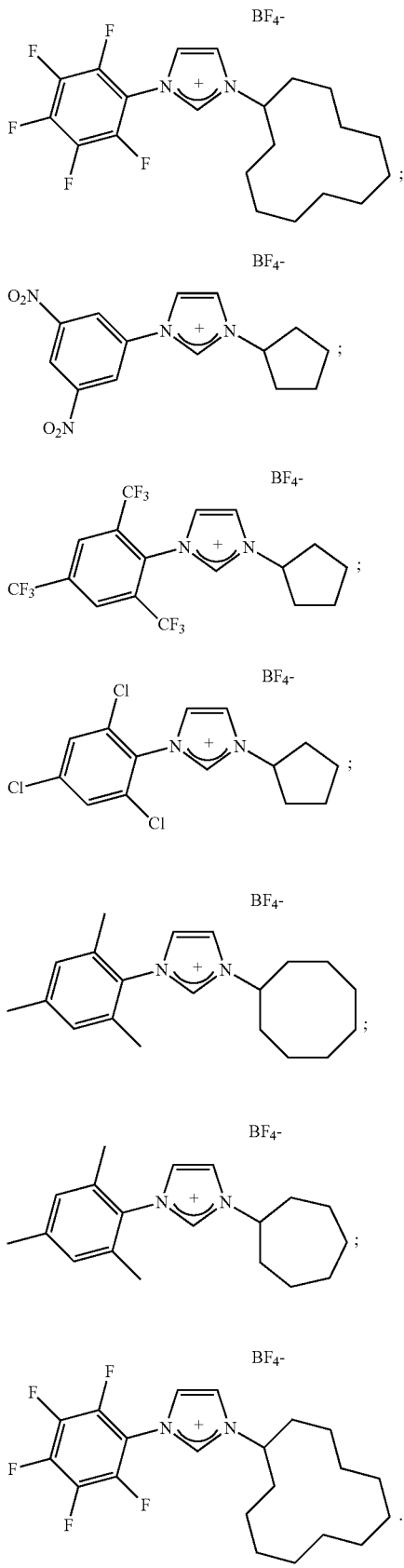

In general the applicants synthesized asymmetric imidazolium salts of formula 1S

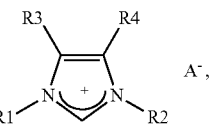

in which R1 is an aromatic group, R2 is a cyclic secondary aliphatic alkyl group, R3 and R4 are selected independently of one another from the group consisting of hydrogen, a halide and an alkyl group, and A⁻ is an anion.

R1 can notably be 2,4,6-trimethylphenyl, 3,5-dinitrophenyl, 2,4,6-tris(trifluoromethyl)phenyl, 2,4,6-trichlorophenyl, or hexafluorophenyl.

R2 can notably be cyclopentyl, cyclohexyl, cycloheptyl, cyclooctyl, cyclodecyl, cyclododecyl, or cyclopentadecyl.

R3 and R4 can each be hydrogen. R3 and R4 can also be halides (for example a chlorine atom or alkyl halides). R3 and R4 can also be alkyl groups (for example methyl, ethyl, propyl or isopropyl).

The anion A⁻ can notably be a tetrafluoroborate anion, a hexafluorophosphate anion, an acetate anion, a hexafluoroantimony anion, a tetrakis[(3,5-trifluoromethyl)phenyl]borate anion and a halide anion.

Once the asymmetric imidazolium salt of formula 1S has been synthesized, the ruthenium complexes according to the invention can be synthesized. In fact, the cation of the asymmetric imidazolium salt forms the ligand, namely the N-heterocyclic diaminocarbene ligand (NHC) of the diaminocarbene metal complex of the invention (the alkylidene ruthenium complex).

The experimental conditions for chemical synthesis of the alkylidene ruthenium complexes according to the invention can be the conditions used conventionally in the prior art. Thus, combining the new N-heterocyclic diaminocarbene ligands described above with a ruthenium complex precursor, to form alkylidene ruthenium complexes according to the invention, can be carried out in experimental conditions quite similar to those described in the following scientific works:

Ledoux, N.; Linden, A.; Allaert, B.; Mierde, H. V.; Verpoort, F. *Adv. Synth. Catal.* 2007; 349:1692;

Fournier, P.-A.; Collins, S. K. *Organometallics* 2007, 26, 2945;

Vehlow, K.; Gessler, S.; Blechert, *S. Angew Chem Int Ed* 2007, 46, 8082;

Chung, C. K.; Grubbs, R. H.; *Org Lett.* 2008, 10, 2693;

which may be referred to while reading the present description.

Deprotonation of the imidazolium salt (1 to 3.5 eq.) by a strong base (for example potassium ter-amylate or potassium hexamethyldisilazane, also from 1 to 3.5 eq.) under an inert atmosphere, at room temperature, and in the presence of solvent (toluene for example), makes it possible to generate the free N-heterocyclic diaminocarbene.

After reaction for thirty minutes, a ruthenium complex precursor (1 eq.) is introduced into the reaction mixture. Then the reaction mixture is heated to at least 80° C. for two hours. Finally, purification on silica gel makes it possible to separate the various impurities from the ruthenium complex that has formed.

Ruthenium complex precursor means a complex of the following general formula 1P:

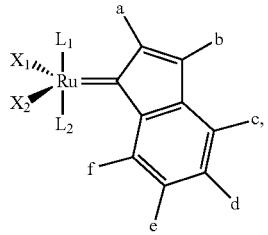
(1P)

in which,

X$_1$ and X$_2$ are anionic ligands,

L$_1$ and L$_2$ are uncharged ligands, preferably tricyclohexylphosphine, and a, b, c, d, e and f are selected independently of one another from the group consisting of a hydrogen atom, an alkyl group and a heteroalkyl group.

It is notably possible to use the ruthenium complex precursor of series M (for example compound M1) from the company Umicore (registered trademark), with the following formula 2P:

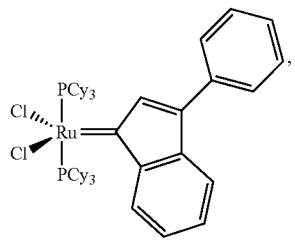
(2P)

in which PCy3 represents tricyclohexylphosphine. This is in fact bis(tricyclohexylphosphine)-3-phenyl-1H-inden-1-ylideneruthenium(II) dichloride.

In other embodiments, other ruthenium complex precursors can be used, for example the complex called first-generation Grubbs catalyst or benzylidene-bis(tricyclohexylphosphine)dichlororuthenium.

In these conditions, the deprotonated imidazolium salt reacts with the ruthenium complex precursor to form a ruthenium complex according to the invention, namely comprising a 1-aryl-3-cycloalkyl-imidazolin-2-ylidene ligand, in which the cycloalkyl group of the 1-aryl-3-cycloalkyl-imidazolin-2-ylidene ligand is a cyclic secondary aliphatic alkyl.

In practice, the ligand(s) L$_1$ and/or L$_2$ of formula 1P is/are substituted with the free N-heterocyclic diaminocarbene.

Thus, when just one of the ligands L$_1$ or L$_2$ is substituted with the free N-heterocyclic diaminocarbene, the complex of the invention can be of the general formula of formula 1,

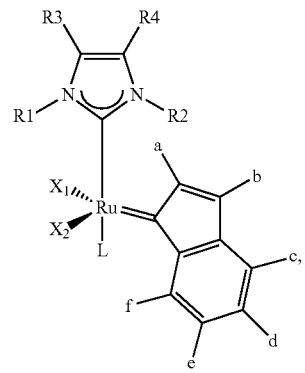
(1)

in which

R1 is an aromatic group,

R2 is a cyclic secondary aliphatic alkyl group,

R3 and R4 are selected independently of one another from the group consisting of a hydrogen atom, a halide and an alkyl group, X$_1$ and X$_2$ are anionic ligands, L is an uncharged ligand, and a, b, c, d, e and f are selected independently of one another from the group consisting of a hydrogen atom, an alkyl group and a heteroalkyl group.

When the two ligands L$_1$ and L$_2$ are each substituted with the free N-heterocyclic diaminocarbene, the complex of the invention can be of the general formula of formula 2:

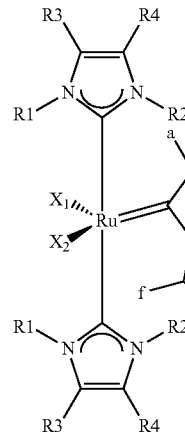
(2)

in which

R1 is an aromatic group,

R2 is a cyclic secondary aliphatic alkyl group,

R3 and R4 are selected independently of one another from the group consisting of a hydrogen atom, a halide and an alkyl group, X$_1$ and X$_2$ are anionic ligands, and a, b, c, d, e and f are selected independently of one another from the group consisting of a hydrogen atom, an alkyl group and a heteroalkyl group.

Generally a mixture of complexes of formula 1 and of formula 2 is obtained, in proportions favouring the complex of formula 1 when the imidazolium salt is used in an amount from about 1 to 1.3 eq., and in proportions favouring the complex of formula 2 when the imidazolium salt is used in an amount from about 2.2 to 3 eq.

To summarize, the ruthenium complexes according to the invention can comprise one or two 1-aryl-3-cycloalkyl-imidazolin-2-ylidene ligands, in which the cycloalkyl group(s) of each 1-aryl-3-cycloalkyl-imidazolin-2-ylidene ligand is a cyclic secondary aliphatic alkyl.

The ruthenium complexes according to the invention comprising a single 1-aryl-3-cycloalkyl-imidazolin-2-ylidene ligand (for example a compound of formula 1 above; 1 eq.) can react with compounds of the styrenyl ether type (about 1.1 to 1.75 eq.) to form ruthenium complexes called chelating ruthenium complexes. This reaction is generally carried out in the presence of a Lewis acid (for example copper(I) chloride; 1.1 to 1.6 eq.) and a solvent (for example dichloromethane), at a temperature of 35° C. for about 5 hours.

The styrenyl ether can be of formula 1H:

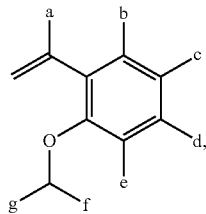

(1H)

in which a, b, c, d, e, f and g are selected independently of one another from the group consisting of a hydrogen atom, an alkyl group and a heteroalkyl group, where f and e optionally form a ring. Preferably, a, b, c, d and e are each a hydrogen atom (H), and f and g are each a methyl group ($CH_3$).

For example the styrenyl ether can be of formula 2H:

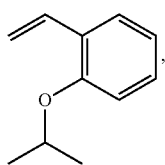

(2H)

or of formula 3H:

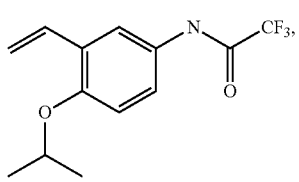

(3H)

More generally the styrenyl ether is of formula 4H:

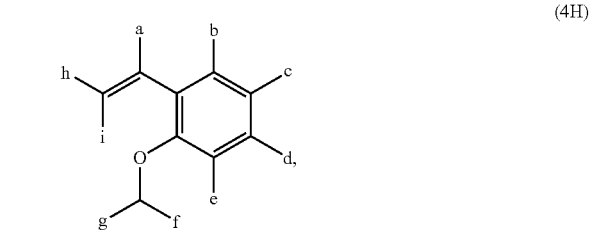

(4H)

in which a, b, c, d, e, f, g, h and i are selected Independently of one another from the group consisting of a hydrogen atom, an alkyl group and a heteroalkyl group.

Thus, the alkylidene ruthenium complex of the invention can be of formula 3:

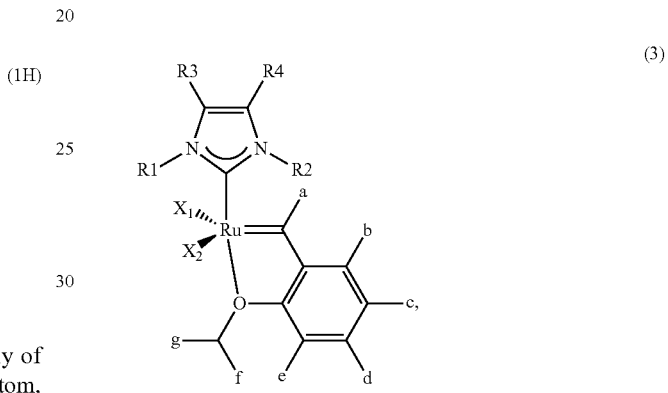

(3)

in which
R1 is an aromatic group,
R2 is a cyclic secondary aliphatic alkyl group,
R3 and R4 are selected independently of one another from the group consisting of a hydrogen atom, a halide and an alkyl group,
$X_1$ and $X_2$ are anionic ligands, and
a, b, c, d, e, f and g are selected independently of one another from the group consisting of a hydrogen atom, an alkyl group and a heteroalkyl group, where f and e optionally form a ring.

In a particular embodiment of the invention and under selected conditions, the applicants also synthesized a ruthenium complex according to the invention of so-called cationic chelating form. The conditions are detailed below.

Deprotonation of the imidazolium salt (2.7 to 3.5 eq.) by a strong base (2.7 to 3.5 eq. of potassium hexamethyldisilazane) under inert atmosphere, at room temperature, and in the presence of solvent (toluene), makes it possible to generate the free N-heterocyclic diaminocarbene.

After reaction for thirty minutes, a ruthenium complex precursor (1 eq.) is added to the reaction mixture. It is the ruthenium complex precursor from Sigma-Aldrich (registered trademark) called "Hoveyda-Grubbs catalyst $1^{st}$ generation" commercially available from the company Sigma-Aldrich Co. This ruthenium complex precursor is dichloro (o-isopropoxyphenylmethylene)(tricyclohexylphosphine) ruthenum(II). The mixture obtained is left to react at a temperature of about 40° C. for about 2 hours.

Following this procedure, the alkylidene ruthenium complex of the invention can be of formula 4:

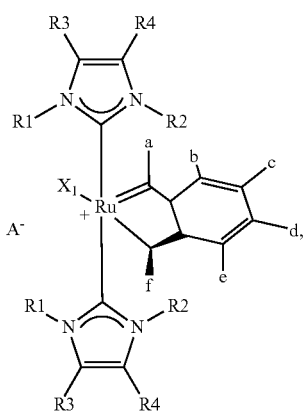

(4)

in which

R1 is an aromatic group,

R2 is a cyclic secondary aliphatic alkyl group,

R3 and R4 are selected independently of one another from the group consisting of a hydrogen atom, a halide and an alkyl group, a, b, c, d, e and f are selected independently of one another from the group consisting of a hydrogen atom, an alkyl group and a heteroalkyl group, $X_1$ is an anionic ligand, and $A^-$ is an anion.

$X_1$ can be a halogen (for example chlorine) and $A^-$ can notably be a tetrafluoroborate anion, a hexafluorophosphate anion, an acetate anion, a hexafluoroantimony anion, a tetrakis(pentafluorophenyl)borate anion and a halide anion.

PRACTICAL EXAMPLES

In the following examples, the $^1H$ (400 MHz), $^{13}C$ (125 MHz), $^{31}P$ (162 MHz), $^{11}B$ (128 MHz) and $^{19}F$ (376 MHz) NMR spectra were recorded on a Brucker ARX 400 Fourier transform spectrometer with proton decoupling for all the nuclei except $^1H$. The chemical shifts (δ) are expressed in parts per million (ppm), in the deuterated solvent stated. The following abbreviations are used to denote signal multiplicity: s (singlet), d (double), t (triplet), q (quadruplet), quin. (quintuplet), sept. (septuplet), m (multiplet), bs (broad singlet).

Moreover, the toluene is dried on a drying column and replaced on a 4 Å molecular sieve before being degassed. The dichloromethane is distilled on calcium hydride.

Analytical thin-layer chromatography was performed on Merck 60F254 silica-coated aluminium plates, using UV light at 254 nm or a solution of $KMnO_4$ at 3% as developer. Purification by column chromatography was performed with silica gel of Merck (registered trademark) type 9385 (230-400 mesh).

A. Synthesis of 1-aryl-3-cycloalkyl-imidazolium-$BF_4^-$ Salts

The aniline (mesitylamine, 40 mmol, 1 eq) and cycloalkylamine (40 mmol, 1 eq) are put in a flask. Then acetic acid (10 mL, 18 mmol, 4.5 eq) is added slowly. The mixture is then stirred for 5 minutes.

Glyoxal (4.6 mL, 40 mmol, 1 eq), formol (3.0 mL, 40 mmol, 1 eq) and acetic acid (10 mL, 18 mmol, 4.5 eq) are put in a flask, and the mixture is heated to 80° C. The mixture of amines prepared previously is then added dropwise to this solution, then the medium is left at 80° C. for the allotted time (from 2 h to 14 h).

Once the reaction is completed, the reaction mixture is cooled to room temperature and then water (20 mL) is added, followed by 40 mL of ethyl acetate (EtOAc). The aqueous phase is extracted three times with 20 mL of ethyl acetate (EtOAc) and then the organic phases are combined and dried over magnesium sulphate ($MgSO_4$), and concentrated under vacuum. Nuclear magnetic resonance (NMR) analysis of the crude reaction product can be used for determining the selectivity of the reaction.

The crude reaction product is then dissolved in 70 mL of dichloromethane ($CH_2Cl_2$) and then 5.15 g of potassium tetrafluoroborate ($KBF_4$) (40 mmol, 1 eq) is added. The mixture is then stirred at room temperature for 3 h. Next, liquid/liquid extraction is carried out, namely water/organic solvent extraction (here $H_2O/CH_2Cl_2$). For this, 20 mL of water is added, the phases are separated, the aqueous phase is washed three times with 20 mL of dichloromethane ($CH_2Cl_2$). The organic phases are then combined, dried over magnesium sulphate ($MgSO_4$), and concentrated under vacuum. Then 40 mL of ethyl acetate (EtOAc) is added to the resultant brown oil and then the mixture is treated with ultrasound for 5 minutes. A solid forms, which is filtered on a frit, then washed with ethyl acetate (EtOAc) to give the desired 1-aryl-3-cycloalkyl imidazolium.

Each desired 1-aryl-3-cycloalkyl imidazolium salt was submitted to NMR analysis and was confirmed by crystallographic analysis. The data from NMR analysis of two desired 1-aryl-3-cycloalkyl imidazolium salts are presented below.

A1. 5-cyclopentyl-2-mesityl-imidazolium Tetrafluoroborate

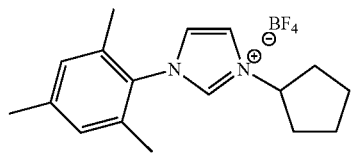

Empirical formula: $C_{17}H_{23}BF_4N_2$
M = 342.18 g/mol
Yield: 35%

Using the general procedure to prepare asymmetric imidazolium with 3.41 g (40 mmol) of cyclopentylamine and 5.6 mL of mesitylamine (40 mmol) leads to 4.80 g (14 mmol, 35%) of asymmetric imidazolium in the form of a white solid.

Selectivity of the reaction:

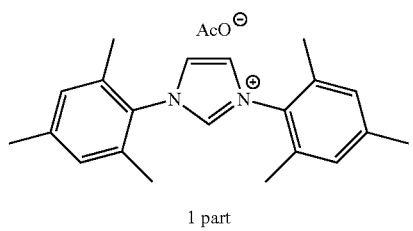

1 part

-continued

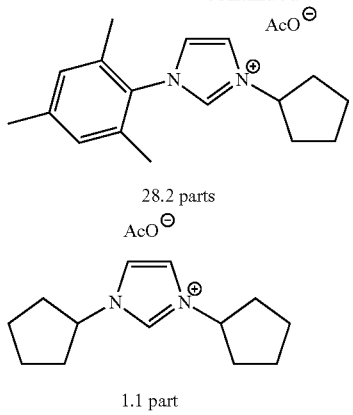

28.2 parts 1.1 part

-continued

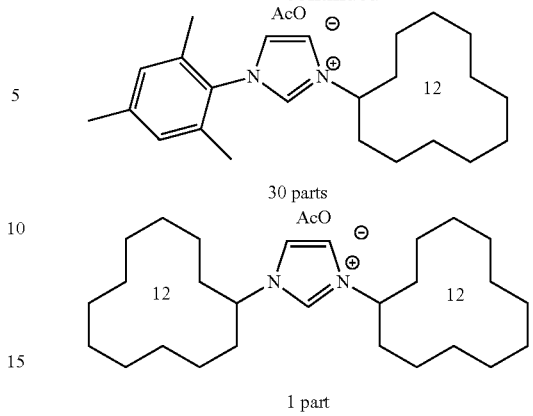

30 parts 1 part $^1$H (400 MHz, CDCl$_3$): 8.82 (t, J=1.73 Hz, 1H$_{im}$); 7.70 (t, J=1.7 Hz, 1H$_{im}$); 7.24 (t, J=1.7 Hz, 1H$_{im}$); 6.97 (s, 2H$_{ar}$); 5.03 (q, J=7.5 Hz, 1H); 2.42 (m, 2H); 2.32 (s, 3H$_{mes}$); 2.00 (s, 6H$_{mes}$); 1.92 (m, 4H); 1.77 (m, 2H)

$^{13}$C (125 MHz, CDCl$_3$): 141.31; 136.6; 134.4 (2C$_{mes}$); 130.8; 129.9 (2C$_{mes}$); 124.3 (C$_{im}$); 121.4 (C$_{im}$); 62.0; 35.6 (2C); 24.0 (2C); 21.2; 17.3 (2C$_{mes}$)

$^{19}$F (376 MHz, CDCl$_3$): −151.98/−152.0 (s)

$^{11}$B (138 MHz, CDCl$_3$): −1.033 (s, BF$_4$)

Tm (melting point): 96° C.

HRMS (high-resolution mass spectrometry) [M$^+$]: Calculated: 255.18612 Found 255.1861.

A2. 5-cyclododecyl-2-mesityl-imidazolium Tetrafluoroborate

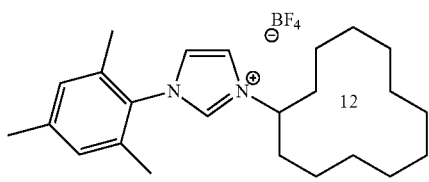

Empirical formula: C$_{24}$H$_{37}$BF$_4$N$_2$
M = 440.37 g/mol
Yield: 62%

Using the general procedure to prepare asymmetric imidazolium with 7.6 mL (40 mmol) of cyclododecylamine and 5.6 mL of mesitylamine (40 mmol) leads to 10.90 g (24.8 mmol, 62%) of asymmetric imidazolium in the form of a white solid.

Selectivity of the reaction:

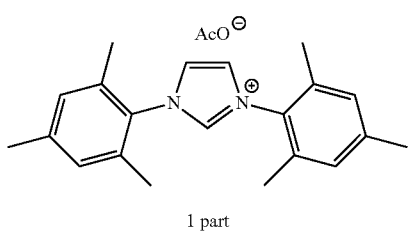

1 part $^1$H (400 MHz, CDCl$_3$): 8.86 (t, J=1.8 Hz, 1H$_{im}$); 7.73 (t, J=1.8 Hz, 1H$_{im}$); 7.27 (t, J=1.8 Hz, 1H$_{im}$); 6.96 (s, 2H$_{ar}$); 4.74 (m, 1H); 2.31 (s, 3H$_{mes}$); 2.11 (m, 2H); 2.00 (s, 6H$_{mes}$); 1.83 (m, 2H); 1.40 (m, 18H)

$^{13}$C (125 MHz, CDCl$_3$): 141.1; 135.9; 134.4 (2C$_{mes}$); 130.9; 129.8 (2C$_{mes}$); 124.2 (C$_{im}$); 121.9 (C$_{im}$); 59.4; 30.2 (2C); 23.7; 23.4 (2C); 23.35 (2C); 23.3 (2C); 21.4 (2C); 21.2; 17.2 (2C$_{mes}$)

$^{19}$F (376 MHz, CDCl$_3$): −151.4/−151.6 (s)

$^{11}$B (138 MHz, CDCl$_3$): −1.033 (s, BF$_4$)

Tm: 177° C.

HRMS [M$^+$]: Calculated: 353.29567 Found 353.2956.

B. Synthesis of Ruthenium Complexes Bearing A 1-aryl-3-cycloalkyl-imidazolin-2-ylidene Ligand Generally, imidazolium salt (1.2 to 1.3 eq.) is weighed in a Schlenk flask in a glove box. Then toluene (for example about 7 mL) is added, followed by potassium ter-amylate (1.2 to 1.3 eq.; for example about 0.70 mL). The mixture is then stirred for 30 minutes. Then the ruthenium complex precursor M1 Umicore (registered trademark) is added (1 eq.; for example about 0.923 g). The Schlenk flask is sealed, and then placed at 80° C. outside of the glove box. After reaction for 3 h, the reaction mixture is concentrated under vacuum and then purified on a silica gel column to isolate the desired ruthenium complexes.

B.1. Synthesis of a Ruthenium Complex (Bearing a Ligand) from a 1-mesityl-3-cyclododecyl Imidazolium Salt of BF$_4^-$ Deprotonation of the 1-mesityl-3-cyclododecyl imidazolium salt of BF$_4$ of formula 95 (1.227 g; 2.79 mmol; 1.28 eq.) by potassium ter-amylate (1.65 mL; 2.80 mmol; 1.1 eq.), under inert atmosphere, at room temperature (RT), and in the presence of toluene (14 mL), makes it possible to generate the free N-heterocyclic diaminocarbene.

After reaction for thirty minutes (30 min), the ruthenium complex precursor (2.02 g; 2.17 mmol; 1 eq.) M1 Umicore (registered trademark) of formula 2P is introduced into the reaction mixture. Then the reaction mixture is heated at 80° C. for two hours. Finally, purification on silica gel makes it possible to separate the various impurities from the ruthenium complex thus formed.

The alkylidene ruthenium complex of formula 1.1 is obtained predominantly (1.352 g; 1.36 mmol; 62%):

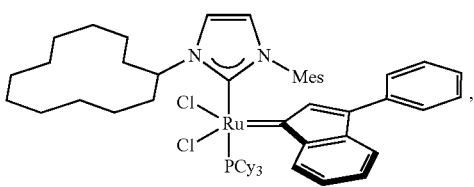

(1.1)

in which PCy₃ represents tricyclohexylphosphine, Mes represents the mesityl group.

NMR:

$^1$H (400 MHz, CDCl$_3$): 8.36 (d, J=7.5 Hz), 7.72 (m, 2Har); 7.50 (m, 1Har); 7.40 (m, 2Har); 7.23 (m, 3Har); 7.15 (m, 2Har); 7.06 (m, 1Har); 6.7 (d, J=2 Hz, 1H); 6.44 (s, 1H); 6.01 (s, 1H); 5.88 (m; 1H$_{C12}$); 2.50-1.12 (m, 64H).

$^{31}$P (162 MHz, CDCl$_3$): 29.06.

However, a minor amount (13%) of the alkylidene ruthenium complex of formula 2.1 is also obtained:

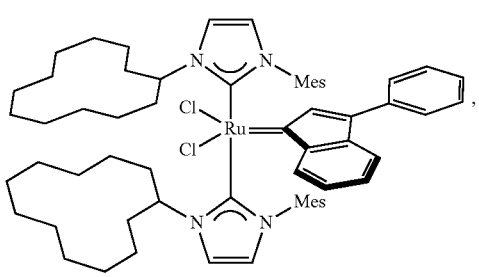

(2.1)

in which Mes represents the mesityl group.

The reaction scheme is shown below:

Reaction scheme II: synthesis of the alkylidene ruthenium complexes of formula 1.1 (62%) and of formula 2.1 (13%).

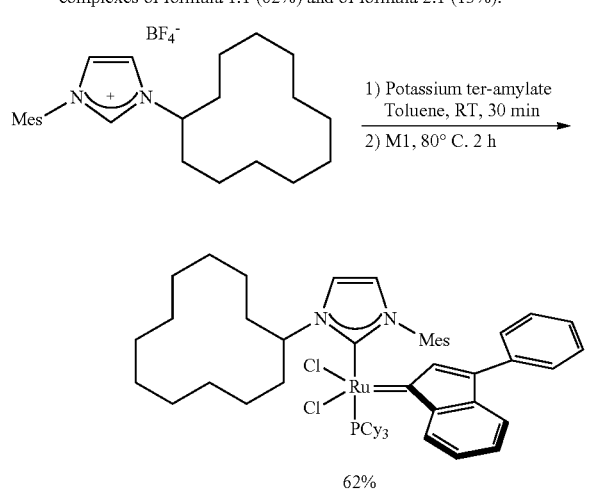

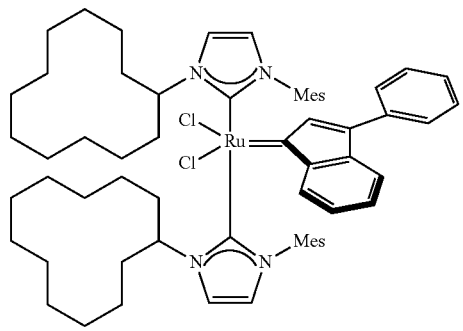

In this reaction scheme, PCy₃ represents tricyclohexylphosphine, Mes represents the mesityl group.

The scheme shows that the predominant product, obtained at a yield of 62%, is the alkylidene ruthenium complex of formula 1.1, and that the minor product, obtained at a yield of 13%, is the alkylidene ruthenium complex of formula 2.1.

The alkylidene ruthenium complex of formula 1.1 was isolated and was submitted to various studies.

Figure 1:
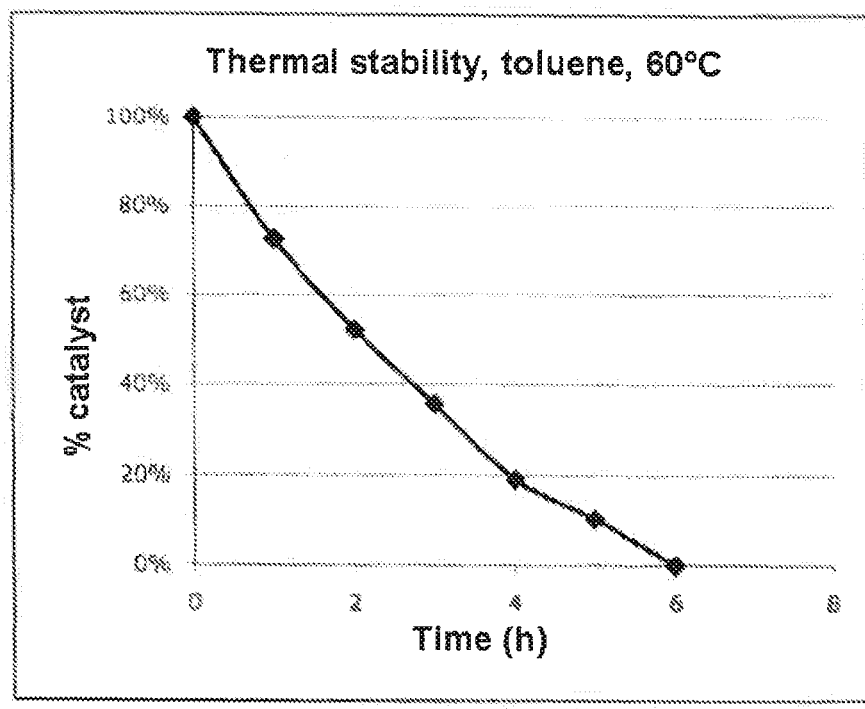
FIG. 1 shows the stability of an alkylidene ruthenium complex according to the invention of formula 1.1 in toluene at 60° C.

Thus, FIG. 1 shows the stability of the alkylidene ruthenium complex of formula 1.1 in toluene at 60° C.

Figure 2:
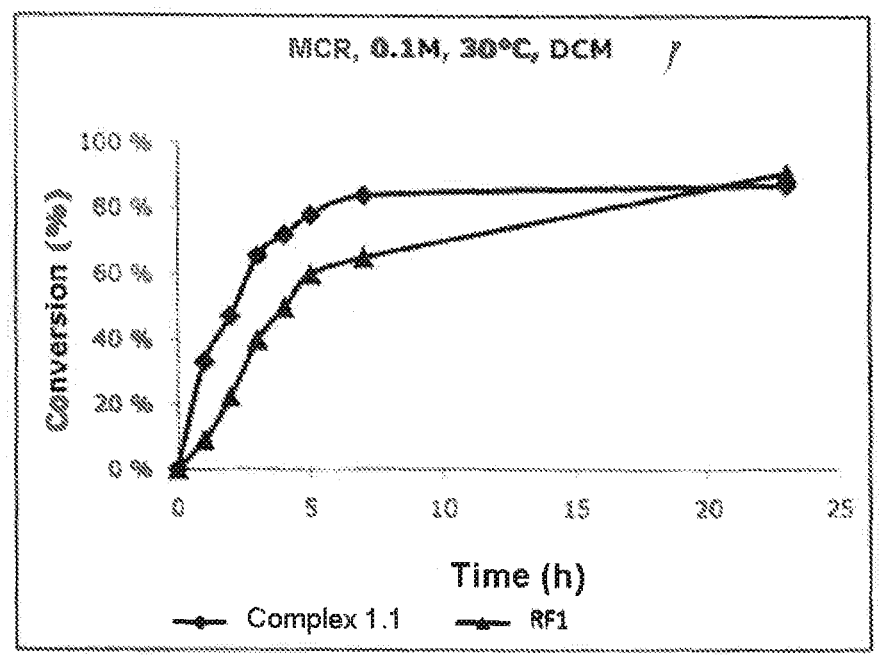
FIG. 2 shows the catalytic activity of an alkylidene ruthenium complex according to the invention of formula 1.1 at 1 mol % in a metathesis cyclization reaction of diethyl 2-allyl-2-(2-methylallyl)malonate at 30° C.

FIG. 2 shows the catalytic activity of the complex of formula 1.1 at 1 mol % in a metathesis cyclization reaction (MCR) of diethyl 2-allyl-2-(2-methylallyl)malonate at 30° C., in dichloromethane (DCM, CH₂Cl₂). The reaction scheme of this MCR is shown below:

Reaction scheme III: MCR of diethyl 2-allyl-2-(2-methylallyl)malonate at 30° C.

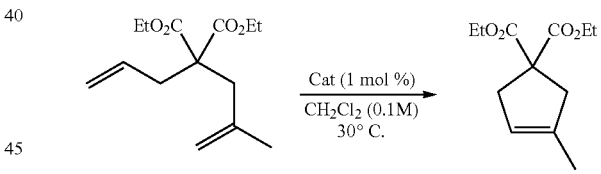

FIG. 2 also shows the catalytic activity of a catalyst commercially available under the name RF1 catMETium (registered trademark) from the company Evonik Degussa GmbH. This is a catalyst bearing a symmetric ligand of the 1,3-bis(2,4,6-mesityl)imidazole type (also called: 1,3-bis(2,4,6-trimethylphenyl)imidazole)). To be precise, it is the catalyst 1,3-bis(2,4,6-trimethylphenyl)imidazol-2-ylidene)(tricyclohexylphosphine)(3-phenylinden-1-ylidene)ruthenium(II) dichloride.

The catalytic activity of the complex according to the invention is higher than that of the catalyst available commercially.

Figure 3:
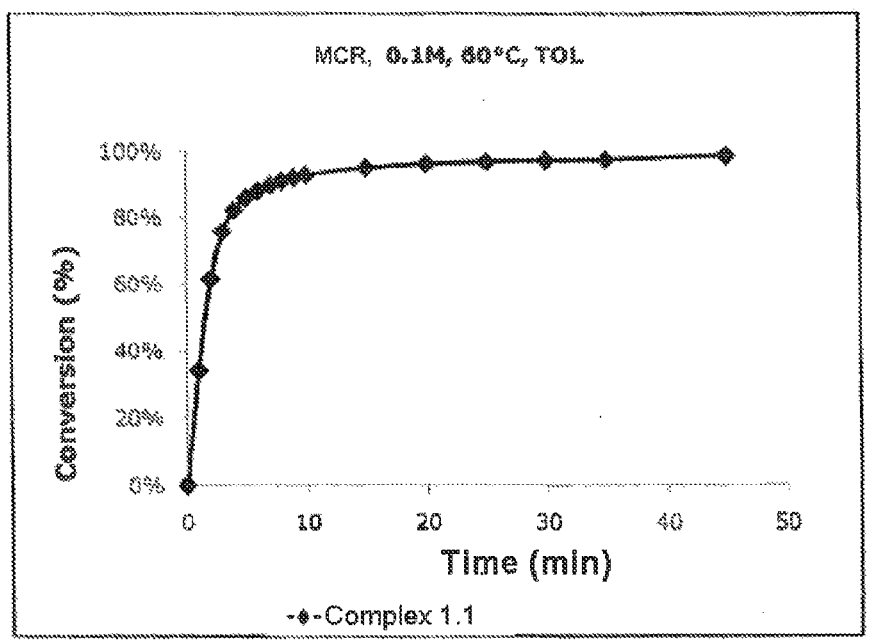
FIG. 3 shows the catalytic activity of an alkylidene ruthenium complex according to the invention of formula 1.1 at 1 mol % in a metathesis cyclization reaction of diethyl 2-allyl-2-(2-methylallyl)malonate at 60° C.

FIG. 3 shows the catalytic activity of the complex of formula 1.1 at 1 mol % in a metathesis cyclization reaction (MCR) of diethyl 2-allyl-2-(2-methylallyl)malonate at 60° C., in toluene (TOL). The reaction scheme of this MCR is shown below:

Reaction scheme IV: MCR of diethyl 2-allyl-2-(2-methylallyl)malonate at 60° C.

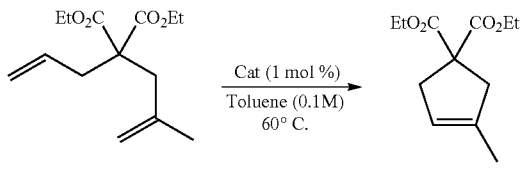

Figure 4:
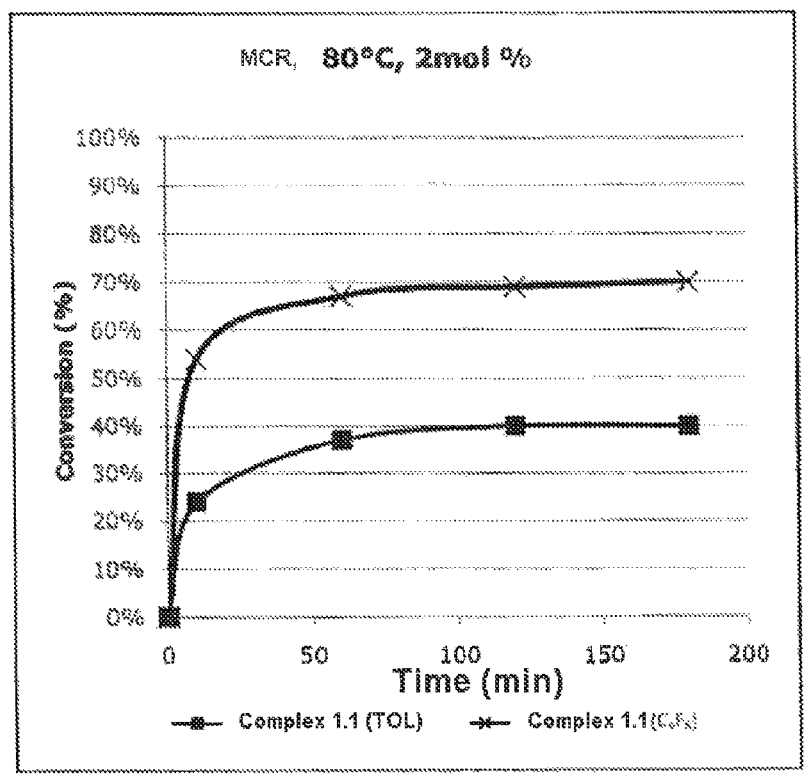
FIG. 4 shows the catalytic activity of an alkylidene ruthenium complex according to the invention of formula 1.1 at 2 mol % in a metathesis cyclization reaction of diethyl 2,2-bis(2-methylallyl)malonate at 80° C.

FIG. 4 shows the catalytic activity of the complex of formula 1.1 at 2 mol % in a metathesis cyclization reaction of diethyl 2,2-bis(2-methylallyl)malonate at 80° C., in microwave treatment at 200 W in toluene (TOL) and in hexafluorobenzene ($C_6F_6$). The reaction scheme of this MCR is shown below:

Reaction scheme V: MCR of diethyl 2,2-bis(2-methylallyl)malonate at 80° C.

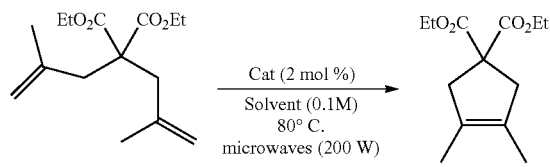

B.2. Synthesis of a Ruthenium Complex (Bearing a Ligand) from a 1-mesityl-3-cyclopentyl Imidazolium Salt of $BF_4^-$ Deprotonation of the 1-mesityl-3-cyclopentyl imidazolium salt of $BF_4^-$ of formula 7S (0.487 g; 1.42 mmol; 1.3 eq.) by potassium ter-amylate (0.82 mL; 1.39 mmol; 1.25 eq.), under inert atmosphere, at room temperature (RT), and in the presence of toluene, makes it possible to generate free N-heterocyclic diaminocarbene.

After reaction for thirty minutes, the ruthenium complex precursor (1.03 g; 1.11 mmol; 1 eq.) M1 Umicore (registered trademark) of formula 2P is introduced into the reaction mixture. Then the reaction mixture is heated at 80° C. for two hours. Finally, purification on silica gel makes it possible to separate the various impurities from the ruthenium complex thus formed.

The alkylidene ruthenium complex of formula 1.2 is obtained predominantly (0.435 g; 0.48 mmol; 43%):

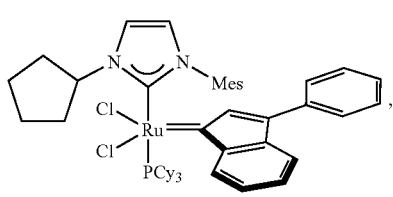

(1.2)

in which $PCy_3$ represents tricyclohexylphosphine and Mes represents the mesityl group.

NMR:
$^1H$ (400 MHz, $CDCl_3$): 8.35 (d, J=7 Hz, 1H); 7.73 (m, 2H); 7.50 (m, 1H); 7.40 (m, 2H); 7.22 (m, 2H); 7.15 (m, 2H); 7.07 (m, 1H); 6.76 (d, J=2 Hz, 1H); 6.44 (s, 1H); 6.03 (m, 2H); 2.27 (m, 2H); 2.35 (m, 3H); 2.03 (m, 4H); 1.89 (m, 9H); 1.77-1.11 (m, 33H).

$^{13}C$ (100 MHz, $CDCl_3$): 290.8; 186.2; 143.5; 140.2; 137.5; 137.4; 136.4; 136.3; 136.25; 136.0; 134.7; 128.9; 128.3; 128.0; 127.5; 127.2; 127.0; 126.5; 126.0; 125.95; 124.2; 119.9; 115.1; 59.0; 30.1; 26.7; 26.4; 22.8; 22.4; 21.0; 20.6; 20.5; 18.5; 18.4.

$^{31}P$ (162 MHz, $CDCl_3$): 29.69

However, a minor amount (12%) of the alkylidene ruthenium complex of formula 2.2 is also obtained:

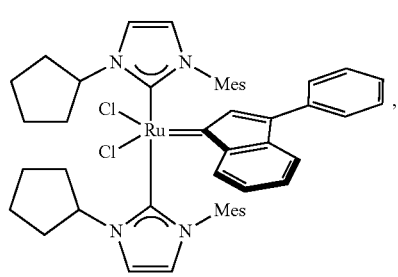

(2.2)

in which Mes represents the mesityl group.
The reaction scheme is shown below:

Reaction scheme VI: synthesis of the alkylidene ruthenium complexes of formula 1.2 (43%) and of formula 2.2 (12%).

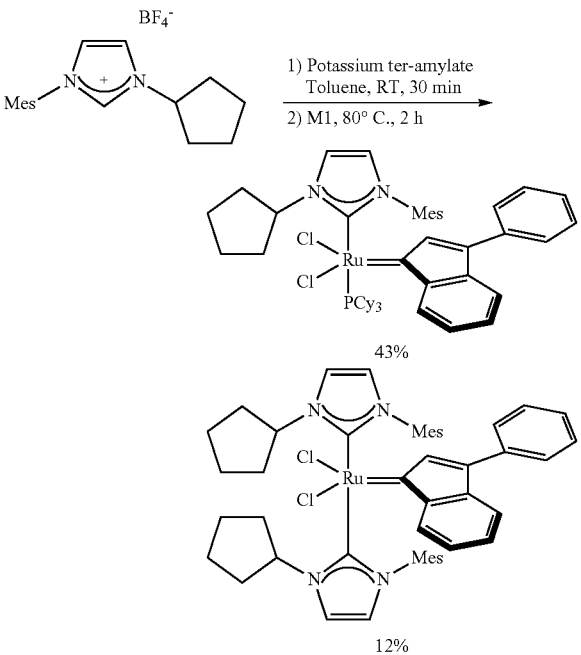

In this reaction scheme, $PCy_3$ represents tricyclohexylphosphine and Mes represents the mesityl group.

The scheme shows that the product obtained predominantly, at a yield of 43%, is the alkylidene ruthenium complex of formula 1.2, and that the minor product, obtained at a yield of 12%, is the alkylidene ruthenium complex of formula 2.2.

The alkylidene ruthenium complex of formula 1.2 was isolated and was submitted to various studies.

Figure 5:
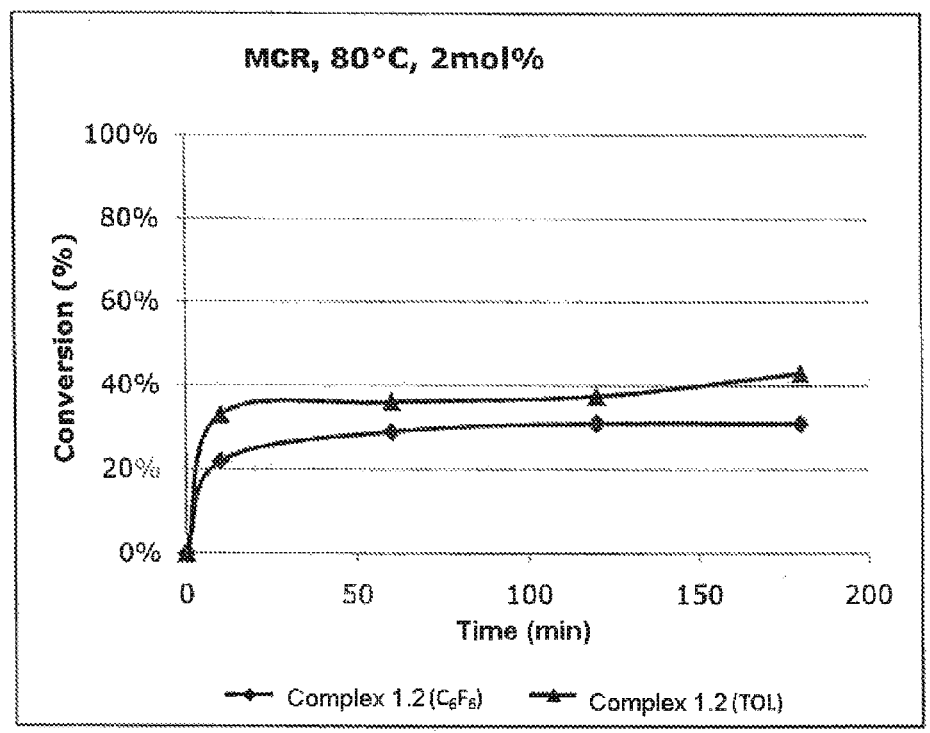
FIG. 5 shows the catalytic activity of an alkylidene ruthenium complex according to the invention of formula 1.2 at 0.2M in a metathesis cyclization reaction of diethyl 2,2-bis(2-methylallyl)malonate at 80° C.

Thus, FIG. 5 shows the catalytic activity of the complex of formula 1.2 at 0.2M in a metathesis cyclization reaction of diethyl 2,2-bis(2-methylallyl)malonate at 80° C., in microwave treatment at 200 W in toluene (TOL) and in hexafluorobenzene (C₆F₆) according to reaction scheme V.

C. Synthesis OF 1-aryl-3-cycloalkyl-imidazolin-2-ylidene Ruthenium Complexes Bearing Two Ligands In general, imidazolium salt (about 3 mmol; about 3 eq.) is weighed in a Schlenk flask in a glove box. Then toluene is added (for example about 0.6 mL), followed by potassium hexamethyldisilazane (0.5M; 3 mmol, 3 eq.; for example about 6 mL). The mixture is then stirred for 30 minutes. Then the ruthenium complex precursor M1 Umicore (registered trademark) is added (1 eq.; 1 mmol; for example 0.92 g). The Schlenk flask is sealed, and then placed at 40° C. outside the glove box. After reaction for 2 h, the reaction mixture is concentrated under vacuum and then purified on a silica gel column to isolate the desired ruthenium complexes.

C.1. Synthesis of a Ruthenium Complex (Bearing 2 Ligands) from a 1-mesityl-3-cyclododecyl Imidazolium Salt of BF₄⁻

Deprotonation of the 1-mesityl-3-cyclododecyl imidazolium salt of BF₄⁻ of formula 9S (2.2 eq.) by potassium hexamethyldisilazane (KHMDS, 1.1 eq.), under inert atmosphere, at room temperature (RT), and in the presence of toluene, makes it possible to generate free N-heterocyclic diaminocarbene.

After reaction for thirty minutes, the ruthenium complex precursor (1 eq.) M1 Umicore (registered trademark) of formula 2P is introduced into the reaction mixture. Then the reaction mixture is heated at 80° C. for two hours. Finally, purification on silica gel makes it possible to separate the various impurities from the ruthenium complex thus formed.

The alkylidene ruthenium complex of formula 2.1 is obtained (at a yield of 65%):

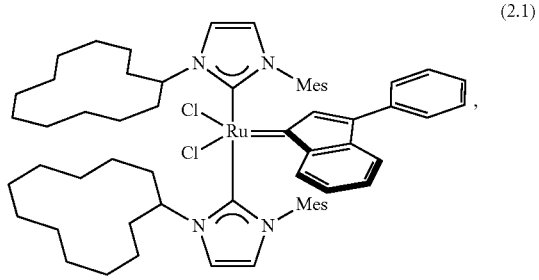

(2.1)

in which Mes represents the mesityl group.

The reaction scheme is shown below:

Reaction scheme VII: synthesis of the alkylidene ruthenium complexes of formula 2.1 (65%).

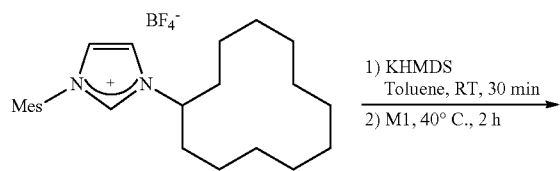

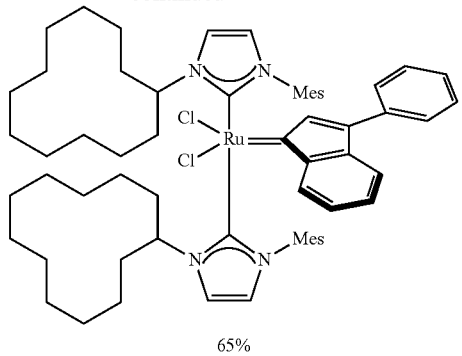

65%

In this reaction scheme, Mes represents the mesityl group.

The scheme shows that the product obtained, at a yield of 65%, is the alkylidene ruthenium complex of formula 2.1.

The alkylidene ruthenium complex of formula 2.1 was isolated and was submitted to various studies.

Figure 6:
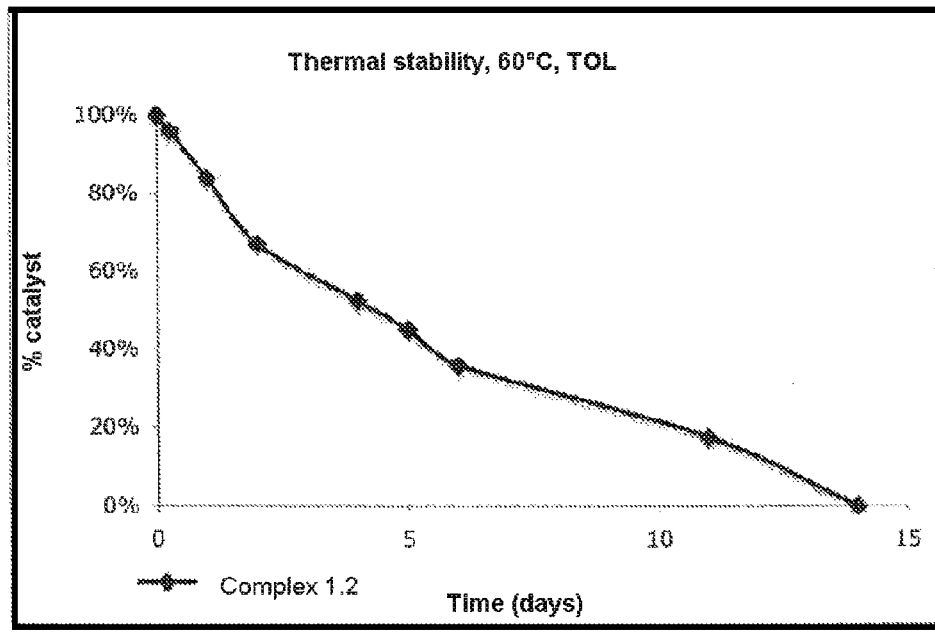
FIG. 6 shows the stability of an alkylidene ruthenium complex according to the invention of formula 2.1 in toluene at 60° C.

Thus, FIG. 6 shows the stability of the alkylidene ruthenium complex of formula 2.1 in toluene at 60° C.

Figure 7:
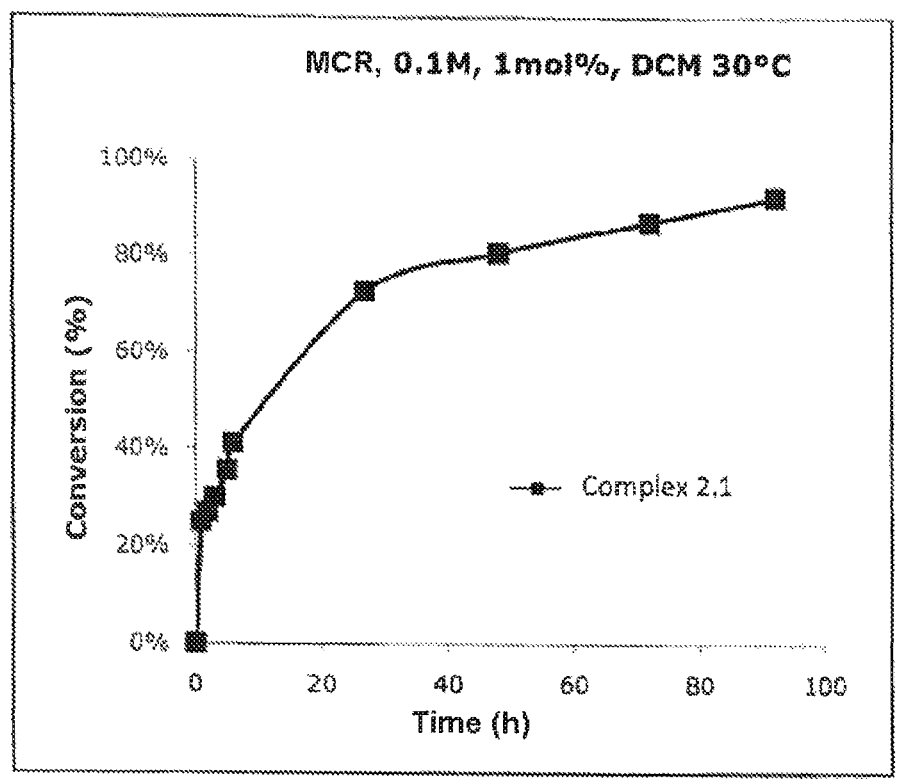
FIG. 7 shows the catalytic activity of an alkylidene ruthenium complex according to the invention of formula 2.1 at 1 mol % in a metathesis cyclization reaction of diethylallymetallylmalonate at 60*C.

FIG. 7 shows the catalytic activity of the complex of formula 2.1 at 1 mol % in a metathesis cyclization reaction of diethyl 2-allyl-2-(2-methylallyl)malonate at 60° C., in microwave treatment at 200 W, in toluene, according to reaction scheme IV.

Figure 8:
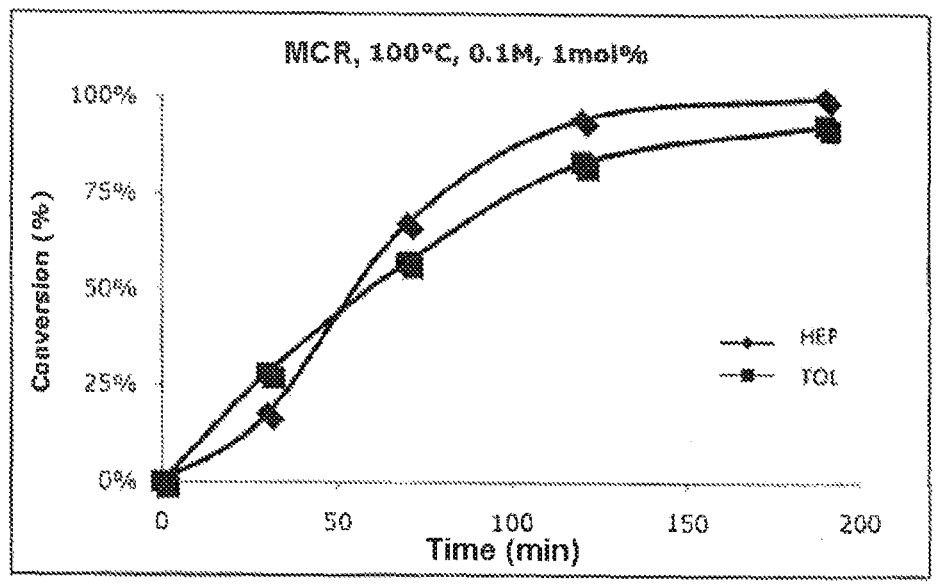
FIG. 8 shows the catalytic activity of an alkylidene ruthenium complex according to the invention of formula 2.1 at 1 mol % in a metathesis cyclization reaction of diethylallymetallylmalonate at 100° C. in toluene and in heptane.

The activity was also measured for this same MCR, but at a temperature of 100° C., and with different solvents. FIG. 8 shows this reaction at 100*C in toluene (TOL) and in heptane (HEP). The catalytic activity in these conditions is higher when the solvent is heptane.

Figure 9:
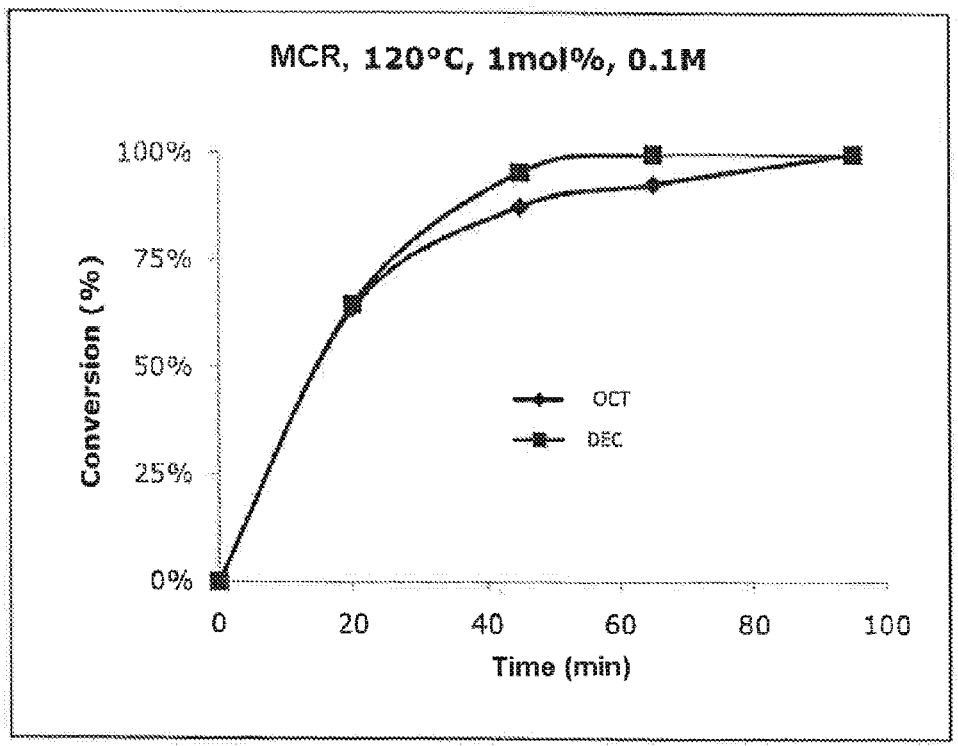
FIG. 9 shows the catalytic activity of an alkylidene ruthenium complex according to the invention of formula 2.1 at 1 mol % in a metathesis cyclization reaction of diethylallymetallylmalonate at 120° C. in octane and in diethyl carbonate.

Moreover, the activity was measured for this same MCR, but at a temperature of 120° C., and with different solvents. FIG. 9 shows this reaction at 120° C. in octane (OCT) and in diethyl carbonate (DEC).

Figure 10:
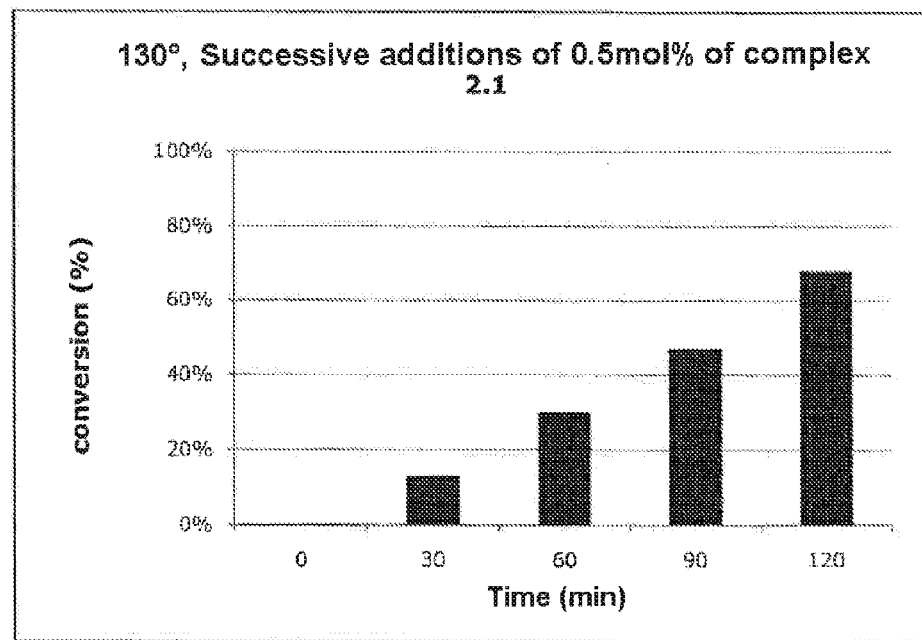
FIG. 10 shows the catalytic activity of an alkylidene ruthenium complex according to the invention of formula 2.1 at 1 mol % in a metathesis cyclization reaction of diethyl 2,2-bis(2-methylallyl)malonate at 130° C. by successive addition.

The activity of the ruthenium complex of formula 2.1 was also analysed for the metathesis cyclization reaction of diethyl 2,2-bis(2-methylally)malonate shown in reaction scheme V, but with a temperature of 130° C. and with successive additions of 0.5 mol % of catalyst (complex of formula 2.1) to give a final amount of 2 mol %. The result is shown in FIG. 10. In these conditions, a conversion of about 70% is reached.

Furthermore, the yield could be increased under other experimental conditions. A deprotonation of the 1-mesityl-3-cyclododecyl imidazolium salt of BF₄ of formula 9S (1.76 g; 4.0 mmol; 2.76 eq.) with potassium hexamethyldisilazane (KHMDS) (8 mL; 0.5M; 4.0 mmol; 2.76 eq.), under an inert atmosphere, at room temperature (RT), and in the presence of anhydrous toluene (3.5 mL), makes it possible to generate the free N-heterocyclic diaminocarbene.

After thirty minutes of reaction, the precursor ruthenium complex (1.34 g; 1.45 mmol; 1 eq.) M1 Umicore (registered trademark) of formula 2P is introduced into the reaction mixture. The reaction mixture is then heated at 40° C. for three hours. Finally, a purification on silica gel makes it possible to separate the various impurities from the ruthenium complex thus formed. It was thus possible to isolate 1.315 g (1.23 mmol; 85%) of complex of formula 2.1.

NMR:
¹H (400 MHz, CDCl₃): 8.11 (d, J=7.5 Hz, 1H); 7.71 (m, 2H); 7.52 (m, 1H); 7.40 (m, 2H); 7.19 (d, J=1.7 Hz, 2H); 7.12 (m; 1H); 7.01 (m, 1H); 6.90 (m, 2H); 6.60 (d, J=1.7 Hz, 2H); 6.22 (m, 4H); 5.83 (bs, 2H); 2.43 (m, 4H); 2.20 (m, 4H); 1.91 (m, 4H); 1.76 (m, 10H); 1.61-1.43 (m, 40H).

¹³C (100 MHz, CDCl₃): 140.2; 137.4; 136.4; 136.3; 136.0; 128.9; 128.3; 128.0; 127.6; 127.3; 127.0; 126.5; 126.0; 124.2; 119.8; 115.1; 59.0; 30.1; 26.7; 26.4; 22.8; 22.4; 21.0; 20.6; 18.5; 18.4.

C.2. Synthesis of a Ruthenium Complex (Bearing Two Ligands) from a 1-mesityl-3-cyclopentyl Imidazolium Salt of BF₄⁻

Deprotonation of the 1-mesityl-3-cyclopentyl imidazolium salt of BF₄⁻ of formula 7S (1.423 g; 4.16 mmol; 2.95 eq.) by potassium hexamethyldisilazane (8.2 mL; 0.5M; 4.1 mmol; 2.95 eq.), under inert atmosphere, at room temperature, and in the presence of anhydrous toluene (3.5 mL), makes it possible to generate free N-heterocyclic diaminocarbene.

After reaction for thirty minutes, the ruthenium complex precursor (1 eq.) M1 Umicore (registered trademark) of formula 2P is introduced into the reaction mixture. Then the reaction mixture is heated at 80° C. for two hours (or at 40° C. for three hours). Finally, purification on silica gel makes it possible to separate the various impurities from the ruthenium complex thus formed.

The alkylidene ruthenium complex of formula 2.2 is obtained (658 mg; 0.75 mmol; 53%):

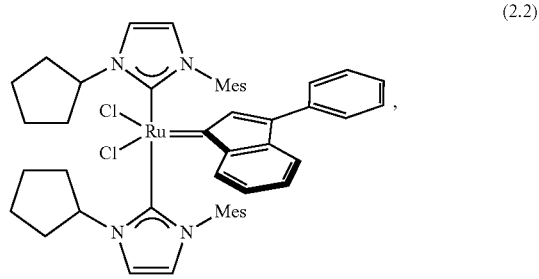

(2.2)

in which Mes represents the mesityl group, and Ind represents the 3-phenyl-indenylidene group.

The reaction scheme is shown below:

Reaction scheme VIII: synthesis of the alkylidene ruthenium complexes of formula 2.1 (65%).

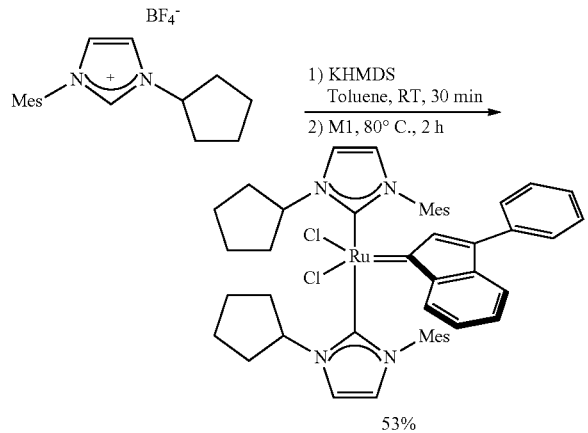

53%

In this reaction scheme, Mes represents the mesityl group. The scheme shows that the product obtained, at a yield of 53%, is the alkylidene ruthenium complex of formula 2.2.

NMR:
¹H (400 MHz, CDCl₃): 8.11 (m, 1H); 7.85 (m, 1H); 7.72 (d, J=7.5 Hz, 2H); 7.45 (m, 3H); 7.20 (m, 4H); 7.06 (m, 2H); 6.88 (m, 2H); 6.66 (m, 2H); 6.51 (m, 2H); 6.26 (bs, 2H): 5.85 (bs, 1H); 2.69 (bs, 4H); 2.58 (bs, 2H); 2.42 (s, 3H); 2.05 (m, 8H); 1.77 (s, 9H); 1.56 (s, 6H); 1.51 (m, 2H).

Figure 11:
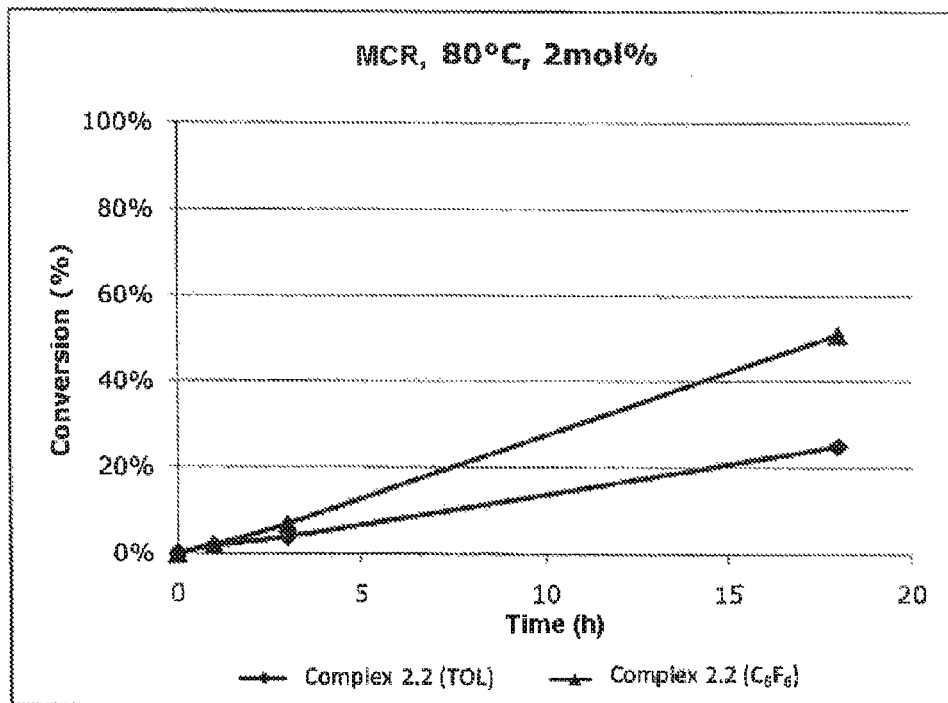
FIG. 11 shows the catalytic activity of an alkylidene ruthenium complex according to the invention of formula 2.2 at 2 mol % in a metathesis cyclization reaction of diethyl 2,2-bis(2-methylallyl)malonate at 80° C.

The alkylidene ruthenium complex of formula 2.2 was isolated and was investigated for its activity. Thus, FIG. 11 shows the catalytic activity of the complex of formula 2.2 at 2 mol % in a metathesis cyclization reaction of diethyl 2,2-bis(2-methylallyl)malonate at 80° C., in microwave treatment at 200 W in toluene (TOL) and in hexafluorobenzene (C₆F6), according to reaction scheme V.

D. Synthesis OF 1-aryl-3-cycloalkyl-imidazolin-2-ylidene Ruthenium Complexes of the Chelating Type Bearing a Ligand

D.1. Synthesis of an Alkylidene Ruthenium Complex of the Chelating Type from the Ruthenium Complex of Formula 1.1 and a Styrenyl Ether of Formula 2H The ruthenium complex of formula 1.1 (0.297 g; 0.300 mmol; 1 eq.) (also called [(5-cyclododecyl-2-mesityl)-imidazo-1-lidene]dichloro(3-phenyl-1H-inden-1-ylidene)(tricyclohexylphosphine)ruthenium) was reacted with the styrenyl ether of formula 2H, namely isopropoxyphenyl-2-propenyl. The reaction is carried out in the presence of dichloromethane (DCM; 3 mL) and copper(I) chloride (CuCl; 35.2 mg; 0.35 mmol; 1.2 eq.), at 35° C. for 5 to 6 hours. After purification on a silica gel column, the desired complex of formula 1.3 was isolated at a yield of 60% (120 mg; 0.178 mmol).

In this way the alkylidene ruthenium complex of formula 1.3 is obtained:

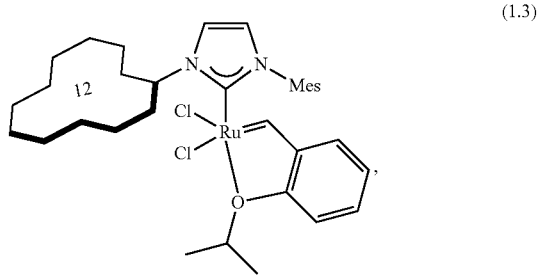

(1.3)

in which Mes represents the mesityl group. The number 12 in formula 1.3 indicates that each cycloalkyl group is a cyclododecyl group.

The reaction scheme is shown below:

Reaction scheme IX: synthesis of the alkylidene ruthenium complexes of formula 1.3 (60%).

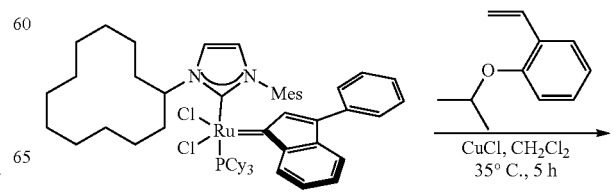

-continued

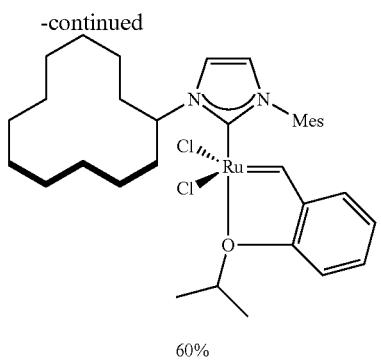

60%

In this reaction scheme, PCy$_3$ represents tricyclohexylphosphine and Mes represents the mesityl group.

The scheme shows that the product obtained, at a yield of 60%, is the alkylidene ruthenium complex of formula 1.3.

The alkylidene ruthenium complex of formula 1.3 was isolated.

NMR:
$^1$H (400 MHz, CDCl$_3$): 16.47 (s, 1H); 7.51 (m, 1H); 7.28 (d, J=2 Hz); 7.10 (s, 2H); 7.00 (m, 1H); 6.93 (m, 2H); 6.85 (d, J=2 Hz); 5.67 (sept., J=5.8 HZ, 1H); 5.17 (sept., J=7 Hz, 1H); 2.50 (s, 3H); 2.23 (m, 4H); 2.02 (s, 6H); 1.80 (d, J=5.8 Hz, 6H); 1.75-1.45 (m, 14H)
$^{13}$C (100 MHz, CDCl$_3$): 171.3; 152.3; 144.8; 139.6; 137.7; 137.6; 129.3; 129.0; 124.4; 122.7; 122.4; 120.1; 113.1; 61.1; 30.6; 25.7; 23.2; 23.1; 22.2; 21.6; 18.2

D.2. Synthesis of an Alkylidene Ruthenium Complex of the Chelating Type from the Ruthenium Complex of Formula 1.1 and a Styrenyl Ether of Formula 3H The ruthenium complex of formula 1.1 (243 mg; 0.24 mmol; 1 eq.) was reacted with the styrenyl ether (122 mg; 0.42 mmol; 1.75 eq.) of formula 3H (namely isopropoxyphenyl-2-propenyl-4,4,4-trifluoroacetamide, hence with a heteroalkyl function, namely a trifluoroacetamide function). The reaction is carried out in the presence of dichloromethane (DCM; 3 mL) and copper(I) chloride (CuCl; 38 mg; 0.38 mmol; 1.6 eq.), at a temperature of 35° C. for 5-6 hours.

The alkylidene ruthenium complex of formula 1.4 is obtained:

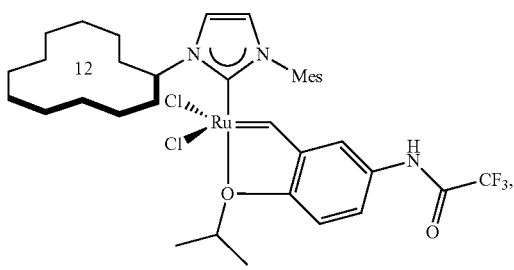

(1.4)

in which Mes represents the mesityl group. The number 12 in formula 1.4 indicates that each cycloalkyl group is a cyclododecyl group.

The reaction scheme is similar to reaction scheme X, but the styrenyl ether of formula 3H (and not the styrenyl ether of 2H) is used.

The complex of formula 1.4 was obtained at a yield of 76% (146 mg; 0.186 mmol).

NMR:
$^1$H (400 MHz, CDCl$_3$): 16.34 (s, 1H); 7.89 (s, 1H); 7.54 (dd, J=2.5 Hz, J=8.8 Hz, 1H); 7.43 (d, J=2.5 Hz, 1H); 7.28 (d, J=2.2 Hz); 7.13 (s, 2H); 6.88 (m, 2H); 5.61 (sept., J=3.3 Hz, 1H); 5.12 (sept., J=6.2 Hz, 1H); 2.55 (s, 3H); 2.23 (m, 4H); 2.01 (s, 6H); 1.78 (d, J=6.2 Hz, 6H); 1.69 (m, 4H); 1.46 (m, 14H).
$^{13}$C (100 MHz, CDCl$_3$): 286.5; 169.4; 154.8; 154.4; 150.1; 144.5; 140.0; 137.4; 137.2; 130.3; 129.2; 124.3; 120.0 (2C); 114.2; 113.1; 75.6; 60.9; 30.5; 25.4; 24.9; 23.0; 22.9; 22.0; 21.5; 21.2; 18.0
$^{19}$F (376 MHz, CDCl$_3$): −75.5

The complex of formula 1.4 was submitted to various studies.

Figure 12:
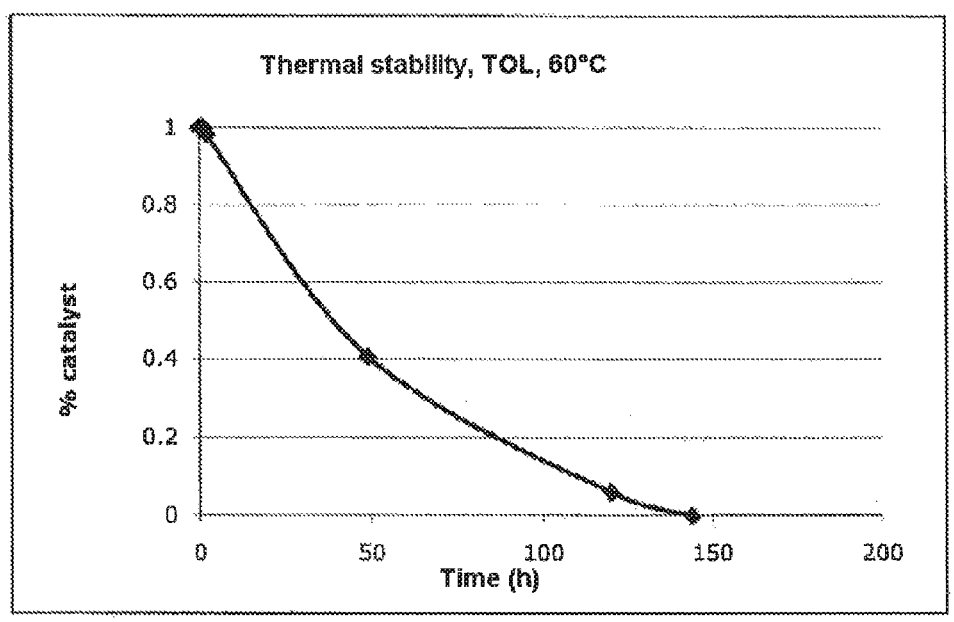
FIG. 12 shows the stability of an alkylidene ruthenium complex according to the invention of formula 1.4 in toluene at 60° C.

Thus, FIG. 12 shows the stability of the alkylidene ruthenium complex of formula 1.4 in toluene at 60° C.

Figure 13:
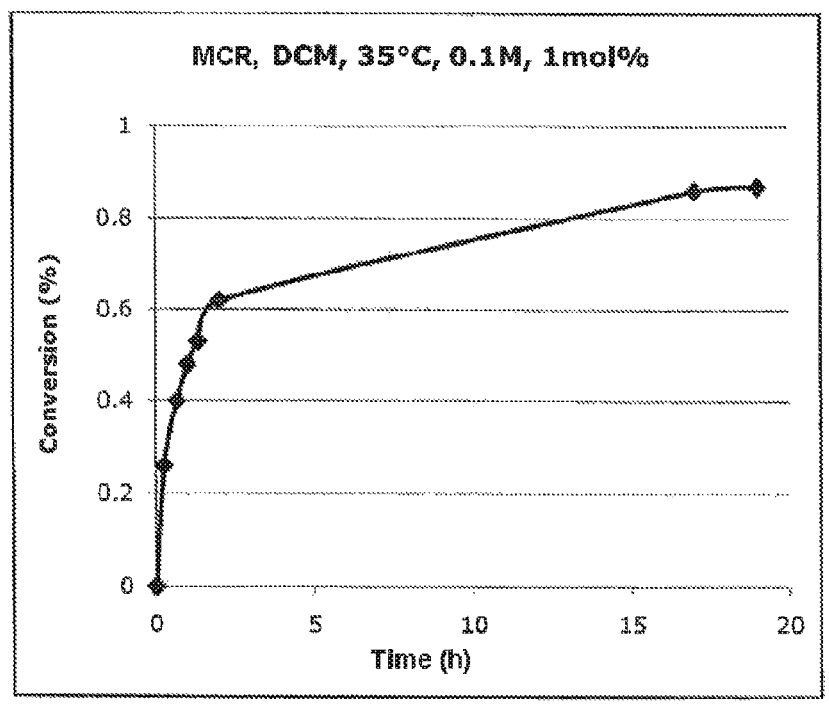
FIG. 13 shows the catalytic activity of an alkylidene ruthenium complex according to the invention of formula 1.4 at 1 mol % in a metathesis cyclization reaction of diethyl 2-allyl-2-(2-methylallyl)malonate at 35° C.

FIG. 13 shows the catalytic activity of the complex of formula 1.4 at 1 mol % in a metathesis cyclization reaction (MCR) of diethyl 2-allyl-2-(2-methylallyl)malonate at 35° C., in dichloromethane (DCM). The reaction scheme of this MCR is shown below:

Reaction scheme X: MCR of diethyl 2-allyl-2-(2-methylallyl)malonate at 35° C.

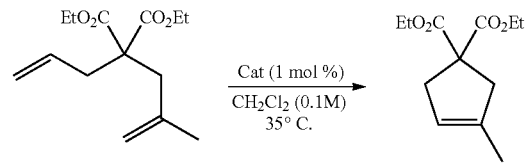

D.3. Synthesis of an Alkylidene Ruthenium Complex of the Chelating Type from the Ruthenium Complex of Formula 1.2 and a Styrenyl Ether of Formula 2H The ruthenium complex of formula 1.2 (0.309 g; 0.344 mmol; 1 eq.) (also called [(5-cyclopentyl-2-mesityl)-imidazo-1-lidene]dichloro(3-phenyl-1H-inden-1-ylidene)(tricyclohexylphospine)ruthenium) was reacted with the styrenyl ether of formula 2H (65 mg; 0.37 mmol; 1.1 eq.). The reaction is carried out in the presence of dichloromethane (DCM; 3.5 mL) and copper(I) chloride (CuCl; 36.8 mg; 0.37 mmol; 1.1 eq.), at 35° C. for 5 hours.

After purification on a silica gel column, the alkylidene ruthenium complex of formula 1.5 is obtained (89 mg; 0.158 mmol; 45%):

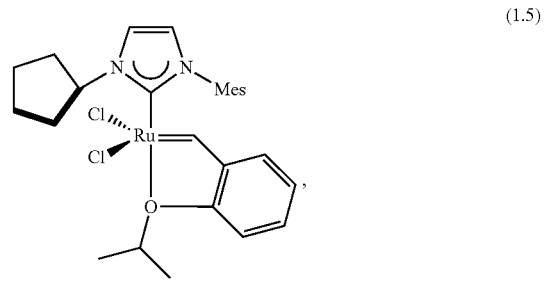

(1.5)

in which Mes represents the mesityl group.

The reaction scheme is shown below:

Reaction scheme XI: synthesis of the alkylidene ruthenium complexes of formula 1.5 (45%).

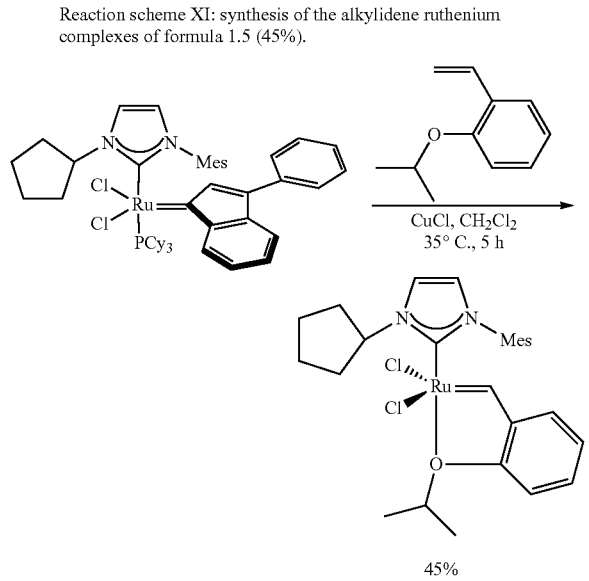

45%

In this reaction scheme, $Cy_3P$ represents tricyclohexylphosphine, Mes represents the mesityl group, and Ph represents a phenyl group.

The scheme shows that the product obtained, at a yield of 45%, is the alkylidene ruthenium complex of formula 1.5.

NMR:

$^1H$ (400 MHz, $CDCl_3$): 16.42 (s, 1H); 7.50 (m, 1H); 7.27 (m, 1H); 7.10 (s, 2H); 7.01 (m, 1H); 6.95 (m, 2H); 6.88 (d, J=2 Hz, 1H); 5.96, (q, J=7.5 Hz, 1H); 5.18 (sept., J=6.21 Hz, 1H);

$^{13}C$ (100 MHz, $CDCl_3$): 172.2; 152.7; 144.5; 139.6; 137.6; 137.4; 129.3; 129.0; 125.0; 122.7; 122.4; 118.5; 113.0; 75.1; 64.2; 34.4; 24.7; 22.0; 21.4; 18.2.

The alkylidene ruthenium complex of formula 1.5 was isolated and was submitted to various studies.

Figure 14:
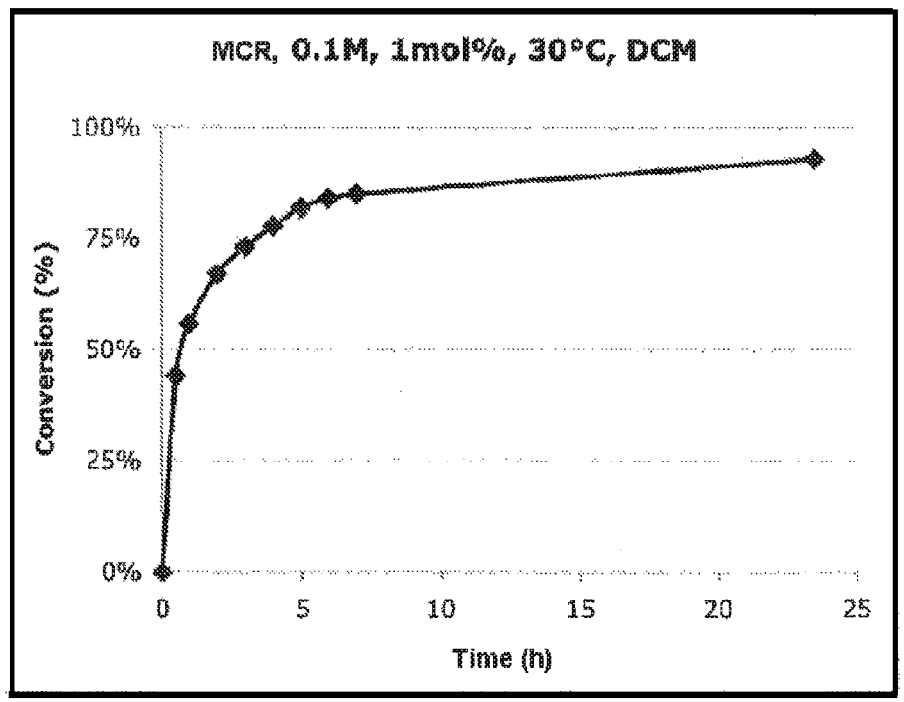
FIG. 14 shows the catalytic activity of an alkylidene ruthenium complex according to the invention of formula 1.5 at 1 mol % in a metathesis cyclization reaction of diethyl 2-allyl-2-(2-methylallyl)malonate at 30° C.
Figure 15:
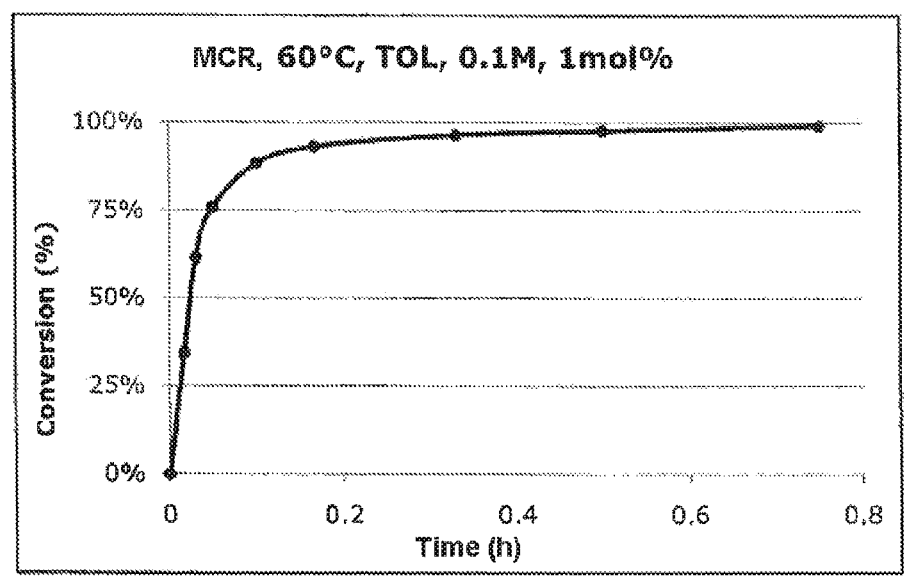
FIG. 15 shows the catalytic activity of an alkylidene ruthenium complex according to the invention of formula 1.5 at 1 mol % in a metathesis cyclization reaction (MCR) of diethyl 2-allyl-2-(2-methylallyl)malonate at 60° C.

Thus, FIG. 14 shows the catalytic activity of the complex of formula 1.5 at 1 mol % in a metathesis cyclization reaction (MCR) of diethyl 2-allyl-2-(2-methylallyl)malonate at 30° C., in dichloromethane (DCM), according to reaction scheme III; and FIG. 15 shows the catalytic activity of the complex of formula 1.5 at 1 mol % in a metathesis cyclization reaction (MCR) of diethyl 2-allyl-2-(2-methylallyl)malonate at 60° C., in toluene (TOL).

D.4. Synthesis of an Alkylidene Ruthenium Complex of the Chelating Type from the Ruthenium Complex of Formula 1.2 and a Styrenyl Ether of Formula 3H The ruthenium complex of formula 1.2 (0.309 g; 0.344 mmol; 1 eq.) was reacted with the styrenyl ether of formula 3H (127 mg; 0.44 mmol; 1.3 eq.). The reaction is carried out in the presence of dichloromethane (DCM; 3.5 mL) and copper(I) chloride (CuCl; 36.8 mg; 0.37 mmol; 1.1 eq.), at 35° C. for 6 hours.

After purification on a silica gel column, the alkylidene ruthenium complex of formula 1.6 is obtained (99 mg; 0.144 mmol; 42%):

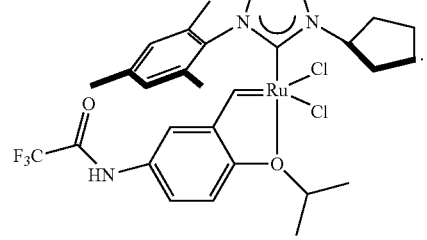

(1.6)

NMR:

$^1H$ (400 MHz, $CDCl_3$): 16.30 (s, H); 7.81 (s, 1H); 7.58 (dd, J=2.2 Hz, I=9.5 Hz, 1H); 7.40 (d, J=2.2 Hz); 7.27 (m, 1H); 6.94 (m, 2H); 5.90 (quin., J=8.0 Hz, 1H); 5.15 (sept., J=6.2 Hz, 1H); 2.69 (m, 2H); 2.55 (s, 3H); 1.95 (m, 12H); 1.78 (d, J=6.2 Hz).

E. Synthesis of a 1-aryl-3-cycloalkyl-imidazolin-2-ylidene Ruthenium Complex of the Cationic Chelating Type Bearing Two Ligands The applicants synthesized cationic chelating ruthenium complexes starting from deprotonation of 1-mesityl-3-cycloalkyl imidazolium salts of $BF_4$.

For this, in a Schlenk flask, the imidazolium salt (about 3 eq.) is dissolved in anhydrous toluene (for example 2 mL). Then potassium hexamethyldisilazane (about 3 eq.) is added to the reaction mixture. The mixture is stirred for 30 minutes at room temperature, then a ruthenium complex precursor of the first-generation Hoveyda-Grubbs type (about 1 eq.) is added. The mixture is left at about 40° C. for 2 to 3 hours and then purified on a silica gel column (by pentane, then $CH_2Cl_2$ and then acetone) to give a solution comprising the desired complex. This solution is evaporated and then dissolved in ethyl acetate. The resultant solid is filtered and washed with ethyl acetate to give the desired cationic chelating complex.

E.1. Synthesis of a First Cationic Chelating Ruthenium Complex Starting from 1-mesityl-3-cyclododecyl Imidazolium Salt of $BF_4^-$ The applicants synthesized a cationic chelating ruthenium complex starting from deprotonation of the 1-mesityl-3-cyclododecyl imidazolium salt of $BF_4^-$ of formula 9S (2.95 mmol; 2.93 eq.) by potassium hexamethyldisilazane (KHMDS, 2.93 eq.), under inert atmosphere, at room temperature (30° C.), and in the presence of toluene, making it possible to generate free N-heterocyclic diaminocarbene.

After reaction for thirty minutes, the ruthenium complex precursor (604 mg; 1 mmol; 1 eq.) from Sigma-Aldrich (registered trademark) called "Hoveyda-Grubbs catalyst 1$^{st}$ generation") or dichloro(o-isopropoxyphenylmethylene)(tricyclohexylphosphine)ruthenium(II) commercially available from the company Sigma-Aldrich Co., is added. The mixture obtained is left to react at a temperature of 40° C. (or 80° C.) for 2-3 hours.

The alkylidene ruthenium complex of formula 4.1 is obtained (564 mg; 0.52 mmol; 52%):

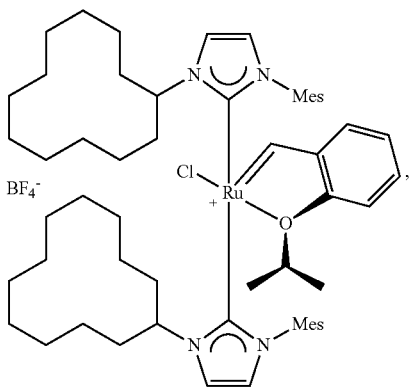

(4.1)

in which Mes represents the mesityl group.

The reaction scheme for synthesis of complex 4.1 is shown below:

Reaction scheme XII: synthesis of the alkylidene ruthenium complexes of formula 4.1 (52%).

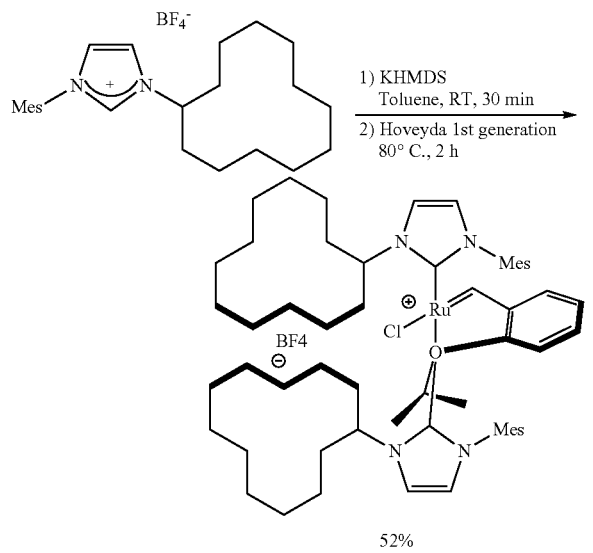

52%

In this reaction scheme, Mes represents the mesityl group.

The scheme shows that the product obtained is the alkylidene ruthenium complex of formula 4.1, at a yield of 52%. NMR:

$^1$H (400 MHz, Acetone D$_6$): 17.12 (s, 1H); 7.83 (d, J=1.8 Hz, 2H); 7.52 (m, 1H); 7.12 (m, 3H); 6.89 (m, 3H); 6.17 (dd, J=1.5 Hz, J=7.4 Hz, 1H); 5.99 (s, 2H); 5.62 (m, 2H); 5.16 (sept., 6.2 Hz, 1H); 2.70 (m, 3H); 2.65 (m, 4H); 2.20 (s, 6H); 2.10 (m, 4H); 1.92 (s, 6H): 1.80-1.40 (m, 39H).

$^{13}$C (100 MHz, Acetone D$_6$): 287.1; 183.4; 158.6; 139.8; 139.6; 136.8; 136.5; 135.2; 131.5; 130.0; 129.6; 126.1; 123.6; 122.8; 122.3; 112.3; 76.9; 61.4; 27.3; 27.1; 27.0; 23.2; 23.1; 23.0; 22.9; 22.5; 22.2; 21.0; 20.5; 18.3; 16.9.

$^{19}$F (376 MHz, CDCl$_3$): −151.98/−152.0 (s).

Appendix 1 shows the crystallographic results for the cationic chelating ruthenium complex of formula 4.1, using the crystallography software CrysAlisPro CCD, Oxford Diffraction Ltd., Version 1.171.35.11.

The alkylidene ruthenium complex of formula 4.1 was isolated and was submitted to various studies.

Thus, FIG. 16 shows the thermal stability of the ruthenium complex of formula 4.1, at 60° C. in toluene (TOL), and at 80° C. in dichloroethane (DCE).

FIG. 17 shows the catalytic activity of the complex of formula 4.1 at 1 mol % in a metathesis cyclization reaction (MCR) of diethyl 2,2-diallylmalonate at 120° C., in xylene (XYL) and in diethyl carbonate (DEC), according to the following reaction scheme:

Reaction scheme XIII: MCR of diethyl 2,2-diallylmalonate at 120° C.

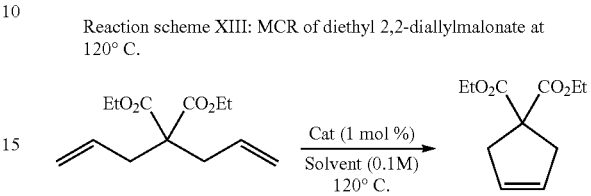

Notably we observe good catalytic activity of the complex of formula 4.1.

E.2. Synthesis of a Cationic Chelating Ruthenium Complex Starting from the 1-mesityl-3-cyclooctyl Imidazolium Salt of BF$_4^-$ The experimental conditions from section E.1. above were repeated using the salt of formula 165 (or 5-cyclooctyl-2-mesityl)-imidazolium tetrafluoroborate) (289 mg; 0.75 mmol; 2.77 eq.) and the ruthenium complex precursor of the first-generation Hoveyda-Grubbs type (163.1 mg; 0.27 mmol; 1 eq.). A complex of formula 4.2 is obtained (85.6 mg; 0.09 mmol; 33%):

(4.2)

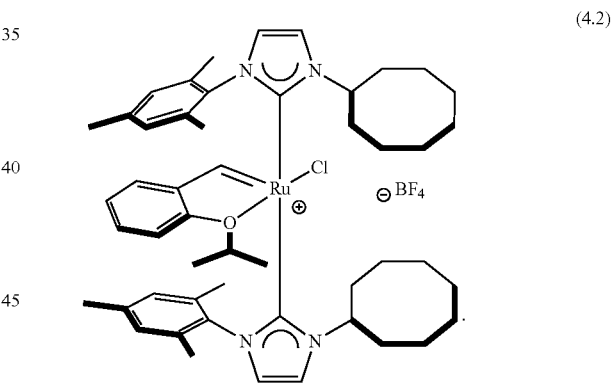

$^1$H (400 MHz, CDCl$_3$): 17.06 (s, 1H); 7.44 (m, 1H); 7.35 (d, J=1.8 Hz, 2H); 7.08 (d, J=8.4 Hz, 1H); 6.85 (s, 2H); 6.67 (d, J=1.8 Hz, 2H); 6.60 (t, J=7.3 Hz, 1H); 5.94 (s, 2H); 5.85 (dd, J=1.5 Hz, 7.7 Hz, 1H); 5.46 (m, 2H); 5.13 (sept., J=6.0 Hz, 1H); 2.44 (m, 8H); 2.19 (s, 6H); 2.12 (m, 2H); 1.91 (s, 6H); 1.76 (m, 18H); 1.32 (d, J=6.0 Hz); 1.05 (s, 6H).

E.3. Synthesis of a Cationic Chelating Ruthenium Complex Starting from the 1-mesityl-3-cycloheptyl Imidazolium Salt of BF$_4^-$ The experimental conditions in section E.1. above were repeated using the salt of formula 17S (or 5-cycloheptyl-2-mesityl)-imidazolium tetrafluoroborate) (221 mg; 0.60 mmol; 3.0 eq.) and the ruthenium complex precursor of the first-generation Hoveyda-Grubbs type (120.0 mg; 0.2 mmol; 1 eq.). A complex of formula 4.3 is obtained (75.3 mg; 0.09 mmol; 40%):

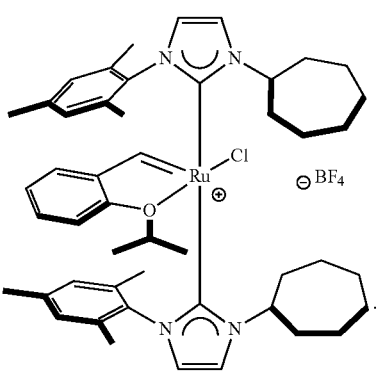

(4.3)

NMR:
¹H (400 MHz, CDCl₃): 17.06 (s, 1H); 7.43 (m, 1H); 7.36 (d, J=1.8 HZ, 2H); 7.05 (d, J=8.4 Hz, 1H); 6.86 (s, 2H); 6.68 (d, J=1.8 Hz, 2H); 6.60 (t, J=7.3 Hz, 1H); 5.93 (s, 2H); 5.83 (dd, J=1.5 Hz, J=7.7 Hz, 1H); 5.53 (q, J=7.0 Hz, 2H); 5.11 (sept., J=6.2 Hz, 1H); 2.61 (m, 4H); 2.30 (m, 2H); 2.20 (s, 6H); 2.09 (m, 4H); 1.90 (s, 6H); 1.84 (m, 12H); 1.34 (d, J=6.2 Hz, 6H); 1.06 (s, 6H).

E.4. Synthesis of a Cationic Chelating Ruthenium Complex Starting from the 1-mesityl-3-cyclohexyl Imidazolium Salt of BF₄⁻

The experimental conditions in section E.1. above were repeated using the salt of formula 8S (or 5-cyclohexyl-2-mesityl)-imidazolium tetrafluoroborate) (215.5 mg; 0.606 mmol; 3.0 eq.) and the ruthenium complex precursor of the first-generation Hoveyda-Grubbs type (122.2 mg; 0.203 mmol; 1 eq.). A complex of formula 4.4 is obtained (55.8 mg; 0.06 mmol; 30%):

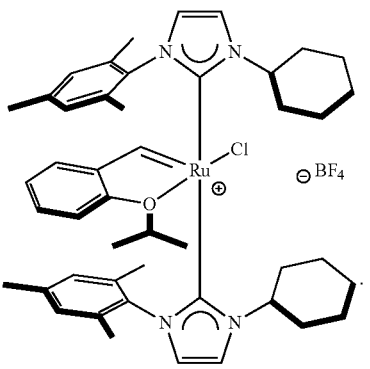

(4.4)

NMR:
¹H (400 MHz, CDCl₃): 17.16 (s, 1H); 7.41 (m, 1H); 7.37 (d, J=1.8 Hz, 2H); 7.00 (d, J=8.4 Hz, 1H); 6.87 (s, 2H); 6.65 (d, J=1.8 Hz, 2H); 6.56 (t, J=7.7 Hz, 1H); 5.95 (s, 2H); 5.77 (dd, J=1.5 Hz, J=7.7 Hz, 1H); 5.18 (m, 2H); 5.06 (sept., J=6.2 Hz, 1H); 2.55 (m, 4H); 2.20 (s, 6H); 2.04 (m, 6H); 1.90 (s, 6H); 1.74 (m, 4H); 1.64 (m, 4H); 1.48 (m, 2H) 1.33 (d, J=6.2 Hz, 6H); 1.02 (s, 6H).

E.5. Synthesis of a Second Cationic Chelating Ruthenium Complex Starting from the 1-mesityl-3-cyclododecyl Imidazolium Salt of BF₄⁻

The experimental conditions in section E.1. above were repeated using the imidazolium salt of formula 9S (361.8 mg; 0.82 mmol; 3.5 eq.) and a ruthenium complex precursor, namely dichloro(4-iso-propoxy-N,N-dimethyl-3-methylene)(tricyclohexylphosphine)ruthenium (147.1 mg; 0.23 mmol; 1 eq.). A complex of formula 4.5 is obtained (79.7 mg; 0.07 mmol; 35%):

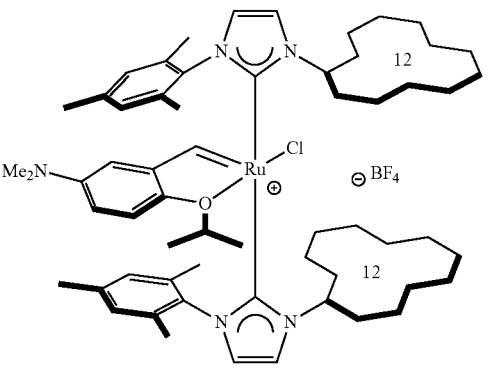

(4.5)

NMR:
¹H (400 MHz, CDCl₃): 17.01 (s, 1H); 7.26 (s, 2H); 6.87 (s, 2H); 6.82 (s, 2H); 6.62 (d, J=1.4 Hz, 2H); 6.01 (s, 2H); 5.50 (m, 2H); 5.28 (s, 1H); 5.29 (s, 2H); 4.97 (sept., J=6.2 Hz, 1H); 2.90 (s, 6H); 2.40 (m, 4H); 2.16 (s, 6H); 2.11 (m, 3H); 1.88 (s, 6H); 1.71 (m, 5H); 1.46 (m, 32H); 1.23 (d, J=6.2 Hz); 1.04 (s, 6H).

The applicants synthesized asymmetric imidazolium salts bearing asymmetric groups R1 and R2 as described above and combined them with ruthenium complex precursors, to provide metal complexes that are very reactive, selective and stable. Since the ligand imidazolin-2-ylidene carbene is stable, this avoids the parasitic reaction of dimerization of the carbene species with itself as described in *NHCs in Synthesis*, S. P. Nolan, Ed., 2006, Wiley-VCH. Accordingly, good yields are observed for synthesis of the target organometallic complexes.

The present invention therefore offers an unpublished route for synthesizing novel metallic complexes from diaminocarbene salts of the 1-aryl-3-cycloalkyl-imidazolin-2-ylidene type.

Moreover, the practical examples demonstrate the stability and reactivity of the complexes of the invention.

APPENDIX 1

Crystallographic results for the cationic chelating ruthenium complex of formula 4.1, using the crystallography software CrysAlisPro CCD, Oxford Diffraction Ltd., Version 1.171.35.11.

| | |
|---|---|
| Identification code | mr129 |
| Empirical formula | C63 H96 B Cl3 F4 N4 O2 Ru |
| Formula weight | 1235.67 |
| Temperature | 140(2) K |
| Wavelength | 0.71069 A |
| Crystal system, space group | Triclinic, P-1 |
| Unit cell dimensions | a = 10.6391(4) A alpha = 80.702(3) deg. |
| | b = 10.8550(5) A beta = 89.011(3) deg. |
| | c = 28.5762(8) A gamma = 85.609(4) deg. |
| Volume | 3247.2(2) A^3 |
| Z, Calculated density | 2, 1.264 Mg/m^3 |
| Absorption coefficient | 0.420 mm −1 |
| F(000) | 1308 |

APPENDIX 1-continued

| Crystal size | 0.275 × 0.183 × 0.088 mm |
|---|---|
| Theta range for data collection | 2.57 to 27.00 deg. |
| Limiting indices | $-13 <= h <= 13, -13 <= k <= 12, -32 <= l <= 36$ |
| Reflections collected/unique | 24382/13597 [R(int) = 0.0637] |
| Completeness to theta = 27.00 | 95.9% |
| Absorption correction | None |
| Refinement method | Full-matrix least-squares on $F^2$ |
| Data/restraints/parameters | 13597/2/673 |
| Goodness-of-fit on $F^2$ | 0.824 |
| Final R indices [I > 2sigma(I)] | R1 = 0.0938, wR2 = 0.2391 |
| R indices (all data) | R1 = 0.2591, wR2 = 0.2888 |
| Largest diff. peak and hole | 1.165 and $-1.064$ e.$\text{A}^{-3}$ |

Atomic coordinates ($\times 10^4$) and equivalent isotropic displacement parameters ($\text{A}^2 \times 10^3$) for mr129. U(eq) is defined as one third of the trace of the orthogonalized Uij tensor.

| | x | y | z | U(eq) |
|---|---|---|---|---|
| C(61) | 4732(18) | 3218(17) | 8943(7) | 235(9) |
| Cl(2) | 4331(7) | 2693(7) | 9504(2) | 310(4) |
| Cl(3) | 5684(6) | 4269(6) | 8782(3) | 308(4) |
| C(71) | 6024(16) | 5850(17) | 5495(7) | 207(7) |
| C(72) | 6890(20) | 6770(20) | 5651(10) | 306(13) |
| O(71) | 7823(17) | 7650(18) | 5498(6) | 283(7) |
| C(73) | 8540(20) | 8430(20) | 5699(9) | 256(10) |
| C(74) | 9570(16) | 9564(17) | 5632(7) | 207(7) |
| B(1) | 7151(15) | 6433(15) | 7058(6) | 101(4) |
| F(1) | 6340(6) | 5757(7) | 6905(2) | 143(3) |
| F(2) | 7308(6) | 6329(6) | 7511(2) | 120(2) |
| F(3) | 6936(12) | 7680(8) | 6842(3) | 209(5) |
| F(4) | 8302(7) | 6125(10) | 6827(2) | 194(4) |
| Ru(1) | 1414(1) | 290(1) | 7994(1) | 86(1) |
| Cl(1) | 2888(3) | 1592(3) | 8214(1) | 109(1) |
| N(1) | 3505(13) | $-2023(10)$ | 8181(3) | 123(5) |
| N(2) | 3766(10) | $-906(9)$ | 7510(3) | 88(3) |
| N(3) | 79(8) | 2803(9) | 7532(3) | 80(3) |
| N(4.) | $-791(11)$ | 2333(12) | 8199(3) | 113(5) |
| O(1) | $-22(5)$ | $-1000(6)$ | 7856(2) | 88(2) |
| C(1) | 973(10) | $-366(10)$ | 8589(3) | 124(5) |
| C(2) | 73(11) | $-1288(10)$ | 8676(3) | 116(5) |
| C(3) | $-311(13)$ | $-1836(12)$ | 9125(3) | 165(7) |
| C(4) | $-1207(14)$ | $-2736(13)$ | 9173(4) | 182(8) |
| C(5) | $-1710(12)$ | $-3081(11)$ | 8767(4) | 136(5) |
| C(6) | $-1362(9)$ | $-2516(9)$ | 8311(3) | 96(4) |
| C(7) | $-446(9)$ | $-1613(9)$ | 8277(3) | 98(4) |
| C(8) | $-459(10)$ | $-1316(12)$ | 7396(2) | 95(4) |
| C(9) | $-910(20)$ | $-258(18)$ | 7142(6) | 316(17) |
| C(10) | 415(18) | $-1800(30)$ | 7156(6) | 360(20) |
| C(11) | 3567(14) | 97(14) | 7099(4) | 126(5) |
| C(12) | 4280(20) | 1172(16) | 7096(5) | 168(7) |
| C(13) | 5560(13) | 870(11) | 7116(4) | 104(4) |
| C(14) | 6168(18) | 2150(11) | 6975(5) | 166(7) |
| C(15) | 6214(14) | 2688(12) | 6492(6) | 145(6) |
| C(16) | 6850(12) | 1836(15) | 6185(5) | 144(5) |
| C(17) | 6384(17) | 2190(20) | 5638(8) | 235(12) |
| C(18) | 5260(30) | 1586(19) | 5551(6) | 254(14) |
| C(19) | 4968(19) | 336(19) | 5661(5) | 175(7) |
| C(20) | 3784(15) | $-162(19)$ | 5747(4) | 163(6) |
| C(21) | 3142(16) | 170(20) | 6196(6) | 240(11) |
| C(22) | 3670(13) | $-477(14)$ | 6630(4) | 162(7) |
| C(23) | 3009(9) | $-1039(10)$ | 7895(4) | 81(3) |
| C(24) | 4735(13) | $-1815(11)$ | 7555(4) | 109(5) |
| C(25) | 4596(15) | $-2555(15)$ | 7980(7) | 155(8) |
| C(26) | 3066(11) | $-2597(11)$ | 8646(4) | 139(6) |
| C(27) | 2304(11) | $-3588(12)$ | 8682(4) | 147(6) |
| C(28) | 1945(14) | $-4160(13)$ | 9127(5) | 185(8) |
| C(29) | 2313(17) | $-3736(17)$ | 9526(5) | 241(12) |
| C(30) | 3110(15) | $-2779(16)$ | 9493(4) | 229(11) |
| C(31) | 3521(14) | $-2192(14)$ | 9041(4) | 186(8) |
| C(32) | 1960(11) | $-4131(11)$ | 8238(5) | 154(6) |
| C(33) | 1820(18) | $-4320(20)$ | 10019(5) | 324(17) |
| C(34) | 4371(12) | $-1138(12)$ | 9007(4) | 193(8) |
| C(35) | 891(9) | 2819(10) | 7105(3) | 83(3) |
| C(36) | 1961(10) | 3598(14) | 7097(3) | 110(4) |
| C(37) | 1648(9) | 4896(11) | 7111(4) | 93(4) |
| C(38) | 2870(9) | 5634(11) | 6953(4) | 110(4) |
| C(39) | 3161(10) | 5797(12) | 6450(4) | 122(5) |
| C(40) | 2192(13) | 6541(13) | 6125(5) | 158(6) |
| C(41) | 2217(14) | 6254(18) | 5602(5) | 173(7) |
| C(42) | 1756(15) | 5010(16) | 5550(4) | 142(5) |
| C(43) | 475(11) | 4846(15) | 5658(3) | 119(5) |
| C(44) | 53(14) | 3507(12) | 5763(3) | 125(5) |
| C(45) | 622(14) | 2753(12) | 6198(4) | 146(5) |
| C(46) | 58(11) | 3120(11) | 6648(3) | 113(4) |
| C(47) | 116(9) | 1899(9) | 7906(3) | 71(3) |
| C(48) | $-1333(13)$ | 3480(15) | 8003(5) | 121(6) |
| C(49) | $-795(10)$ | 3749(12) | 7586(3) | 88(4) |
| C(50) | $-1184(11)$ | 1680(12) | 8656(3) | 130(5) |
| C(51) | $-2218(11)$ | 967(12) | 8669(3) | 136(6) |
| C(52) | $-2630(13)$ | 404(14) | 9114(4) | 174(8) |
| C(53) | $-2018(15)$ | 492(16) | 9531(3) | 203(9) |
| C(54) | $-960(15)$ | 1227(16) | 9497(4) | 237(11) |
| C(55) | $-552(13)$ | 1836(14) | 9066(3) | 176(8) |
| C(56) | $-2931(10)$ | 867(11) | 8224(3) | 113(4) |
| C(57) | $-2438(18)$ | $-251(18)$ | 9999(4) | 283(14) |
| C(58) | 508(13) | 2690(14) | 9037(3) | 211(9) |

The invention claimed is:

1. Alkylidene ruthenium complex comprising a 1-aryl-3-cycloalkyl-imidazoline-2-ylidene ligand, characterized in that the cycloalkyl group of said 1-aryl-3-cycloalkyl-imidazoline-2-ylidene ligand is a cyclic secondary aliphatic alkyl.

2. Alkylidene ruthenium complex according to claim 1, in which said complex is of general formula selected from the group consisting of formula 1,

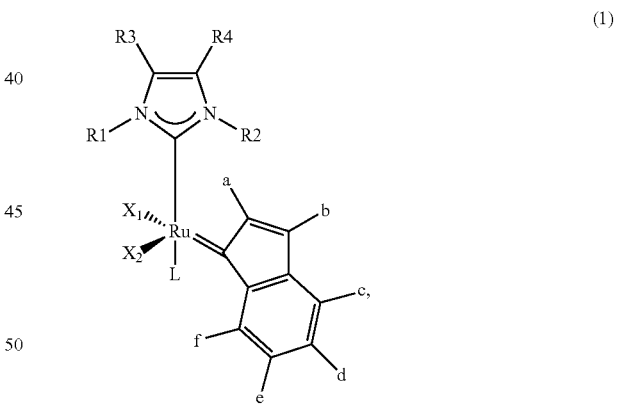

in which

R1 is an aromatic group,

R2 is a cyclic secondary aliphatic alkyl group,

R3 and R4 are selected independently of one another from the group consisting of a hydrogen atom, a halide and an alkyl group, $X_1$ and $X_2$ are anionic ligands, L is an uncharged ligand, and a, b, c, d, e and f are selected independently of one another from the group consisting of a hydrogen atom, an alkyl group and a heteroalkyl group;

of formula 2:

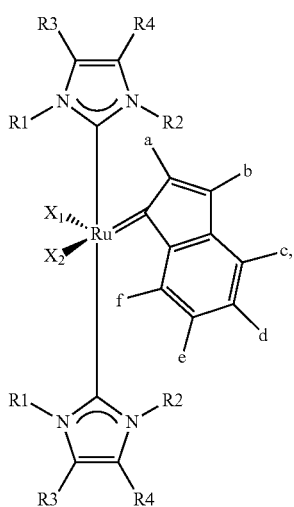
(2)

in which
R1 is an aromatic group,
R2 is a cyclic secondary aliphatic alkyl group,
R3 and R4 are selected independently of one another from the group consisting of a hydrogen atom, a halide and an alkyl group,
$X_1$ and $X_2$ are anionic ligands, and
a, b, c, d, e and f are selected independently of one another from the group consisting of a hydrogen atom, an alkyl group and a heteroalkyl group;

of formula 3:

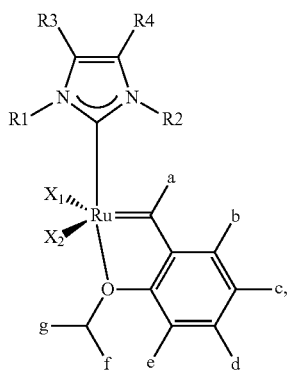
(3)

in which
R1 is an aromatic group,
R2 is a cyclic secondary aliphatic alkyl group,
R3 and R4 are selected independently of one another from the group consisting of a hydrogen atom, a halide and an alkyl group,
$X_1$ and $X_2$ are anionic ligands, and
a, b, c, d, e, f and g are selected independently of one another from the group consisting of a hydrogen atom, an alkyl group and a heteroalkyl group;

and of formula 4:

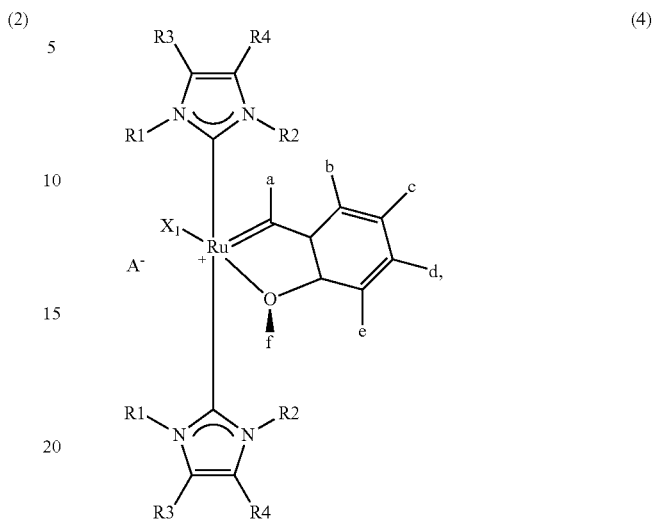
(4)

in which
R1 is an aromatic group,
R2 is a cyclic secondary aliphatic alkyl group,
R3 and R4 are selected independently of one another from the group consisting of a hydrogen atom, a halide and an alkyl group,
a, b, c, d, e and f are selected independently of one another from the group consisting of a hydrogen atom, an alkyl group and a heteroalkyl group,
$X_1$ is an anionic ligand, and
$A^-$ is an anion.

3. Alkylidene ruthenium complex according to claim 2, in which R1 is selected from the group consisting of 2,4,6-trimethylphenyl, 3,5-dinitrophenyl, 2,4,6-tris(trifluoromethyl)phenyl, 2,4,6-trichlorophenyl, and hexafluorophenyl.

4. Alkylidene ruthenium complex according to claim 2, in which R2 is selected from the group consisting of cyclopentyl, cyclohexyl, cycloheptyl, cyclooctyl, cyclodecyl, cyclododecyl, and cyclopentadecyl.

5. Alkylidene ruthenium complex according to claim 2, in which R3 and R4 are each a hydrogen atom.

6. A method of catalysing an olefin metathesis reaction, the method comprising adding the alkylidene ruthenium complex according to claim 1 to a reaction mixture.

7. Method of preparing an alkylidene ruthenium complex comprising the following steps:
  a. forming a first reaction mixture by contacting an imidazolium salt of formula 1S:

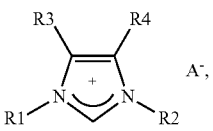
(1S)

in which
R1 is an aromatic group,
R2 is selected from a cyclic secondary aliphatic alkyl group and a heteroalkyl group, R3 and R4 are selected independently of one another from the group consisting of a hydrogen atom, a halide and an alkyl group, and A⁻ is an anion, with a strong base, in a solvent, under inert atmosphere, at room temperature, for at least 30 minutes;
- b. adding a ruthenium complex precursor to the reaction mixture formed in step a., and then heating at a temperature of at least 40° C. for at least 2 hours;
- c. isolating an alkylidene ruthenium complex.

8. Method according to claim 7, in which step b. is carried out at a temperature of about 80° C.

9. Method according to claim 7, in which the ruthenium complex precursor added in step b. is of formula 1P:

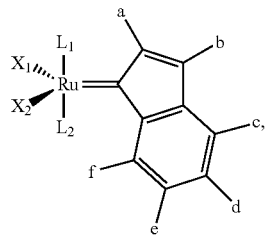

(1P)

in which, $X_1$ and $X_2$ are anionic ligands, $L_1$ and $L_2$ are uncharged ligands, preferably tricyclohexylphosphine, and a, b, c, d, e and f are selected independently of one another from the group consisting of a hydrogen atom, an alkyl group and a heteroalkyl group.

10. Method according to claim 7, further comprising the step of:
- d. forming a second reaction mixture by contacting the alkylidene ruthenium complex isolated in step c. with a styrenyl ether.

11. Method according to claim 7, in which step b. is carried out for at least 3 hours and in which said ruthenium precursor complex is of the so-called first-generation Hoveyda-Grubbs type.

12. Method according to claim 10, in which said styrenyl ether is of formula 4H:

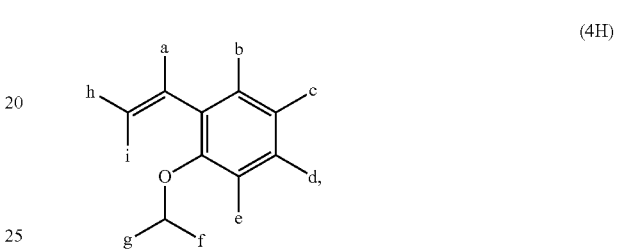

(4H)

in which a, b, c, d, e, f, g, i and h are selected independently of one another from the group consisting of a hydrogen atom, an alkyl group and a heteroalkyl group.

* * * * *